US010456769B2

(12) United States Patent
Wang et al.

(10) Patent No.: US 10,456,769 B2
(45) Date of Patent: Oct. 29, 2019

(54) METHOD OF CONSTRUCTING SEQUENCING LIBRARY

(71) Applicants: BGI Shenzhen, Shenzhen, Guangdong (CN); BGI Shenzhen Co., Limited, Shenzhen, Guangdong (CN)

(72) Inventors: Ou Wang, Shenzhen (CN); Xiaofang Cheng, Shenzhen (CN); Liangying Zou, Shenzhen (CN); Cankun Chang, Shenzhen (CN); Hui Jiang, Shenzhen (CN); Wenwei Zhang, Shenzhen (CN)

(73) Assignee: BGI Shenzhen & BGI Shenzhen Co., Limited (CN)

( * ) Notice: Subject to any disclaimer, the term of this patent is extended or adjusted under 35 U.S.C. 154(b) by 0 days.

(21) Appl. No.: 15/667,841

(22) Filed: Aug. 3, 2017

(65) Prior Publication Data

US 2017/0341051 A1 Nov. 30, 2017

Related U.S. Application Data

(63) Continuation of application No. PCT/CN2016/070789, filed on Jan. 13, 2016.

(30) Foreign Application Priority Data

Feb. 4, 2015 (CN) .......................... 2015 1 0058616

(51) Int. Cl.
*B01J 19/00* (2006.01)
*C12N 15/10* (2006.01)

(52) U.S. Cl.
CPC ...... *B01J 19/0046* (2013.01); *C12N 15/1068* (2013.01); *B01J 2219/00317* (2013.01); *B01J 2219/00587* (2013.01); *B01J 2219/00716* (2013.01); *B01J 2219/00722* (2013.01)

(58) Field of Classification Search
None
See application file for complete search history.

(56) References Cited

U.S. PATENT DOCUMENTS

| 6,401,267 | B1* | 6/2002 | Drmanac | C12Q 1/6874 4/356 |
| 2013/0124100 | A1* | 5/2013 | Drmanac | C12Q 1/6869 702/20 |
| 2013/0130919 | A1* | 5/2013 | Chen | C12Q 1/6874 506/2 |
| 2013/0237432 | A1* | 9/2013 | Li | C12Q 1/6881 506/2 |
| 2016/0177359 | A1* | 6/2016 | Ukanis | C12P 19/34 506/2 |

FOREIGN PATENT DOCUMENTS

| CN | 101932729 A | 12/2010 | |
| CN | 102864498 A | 1/2013 | |
| WO | WO-2013177220 A1 * | 11/2013 | ........... C12Q 1/6874 |
| WO | 2014145820 A2 | 9/2014 | |

OTHER PUBLICATIONS

BMC genomics 15.1 (2014): 184. (Year: 2014).*
Peters et al. (Nature 487.7406 (2012): 190) (Year: 2012).*
Peters et al. 2012 supplementary materials (Year: 2012).*
Peters et al. (Frontiers in genetics 5 (2015): 466; published online Jan. 14, 2015) (Year: 2015).*
Wu et al.( Gigascience 4.1 (2015): 51; published online Nov. 5, 2015) (Year: 2015).*
International Search Report issued for PCT/CN2016/070789 dated Apr. 19, 2016.
Written Opinion of the International Searching Authority issued for PCT/CN2016/070789 dated Apr. 19, 2016.

* cited by examiner

*Primary Examiner* — Tracy Vivlemore
*Assistant Examiner* — Sahana S Kaup
(74) *Attorney, Agent, or Firm* — Westman, Champlin & Koehler, P.A.; Z. Peter Sawicki; Amanda M. Prose

(57) ABSTRACT

Provided is a method of constructing a sequencing library. The method includes 1) providing a single-stranded DNA fragment from a biological sample; 2) subjecting the single-stranded DNA fragment to whole genomic amplification to obtain a whole genome amplification product; 3) fragmenting the whole genome amplification product using a transposase embedded with two adaptors to obtain a fragmented product with two adaptors respectively at two ends; and 4) amplifying the fragmented product with two adaptors respectively at two ends using a tag sequence and a pair of primers to obtain said sequencing library.

18 Claims, 7 Drawing Sheets

Specification includes a Sequence Listing.

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | 1 | 17 | 33 | 49 | 65 | 81 | 97 | 113 | 129 | 145 | 161 | 177 | 193 | 209 | 225 | 241 | 257 | 273 | 289 | 305 | 321 | 337 | 353 | 369 |
| B | 2 | 18 | 34 | 50 | 66 | 82 | 98 | 114 | 130 | 146 | 162 | 178 | 194 | 210 | 226 | 242 | 258 | 274 | 290 | 306 | 322 | 338 | 354 | 370 |
| C | 3 | 19 | 35 | 51 | 67 | 83 | 99 | 115 | 131 | 147 | 163 | 179 | 195 | 211 | 227 | 243 | 259 | 275 | 291 | 307 | 323 | 339 | 355 | 371 |
| D | 4 | 20 | 36 | 52 | 68 | 84 | 100 | 116 | 132 | 148 | 164 | 180 | 196 | 212 | 228 | 244 | 260 | 276 | 292 | 308 | 324 | 340 | 356 | 372 |
| E | 5 | 21 | 37 | 53 | 69 | 85 | 101 | 117 | 133 | 149 | 165 | 181 | 197 | 213 | 229 | 245 | 261 | 277 | 293 | 309 | 325 | 341 | 357 | 373 |
| F | 6 | 22 | 38 | 54 | 70 | 86 | 102 | 118 | 134 | 150 | 166 | 182 | 198 | 214 | 230 | 246 | 262 | 278 | 294 | 310 | 326 | 342 | 358 | 374 |
| G | 7 | 23 | 39 | 55 | 71 | 87 | 103 | 119 | 135 | 151 | 167 | 183 | 199 | 215 | 231 | 247 | 263 | 279 | 295 | 311 | 327 | 343 | 359 | 375 |
| H | 8 | 24 | 40 | 56 | 72 | 88 | 104 | 120 | 136 | 152 | 168 | 184 | 200 | 216 | 232 | 248 | 264 | 280 | 296 | 312 | 328 | 344 | 360 | 376 |
| I | 9 | 25 | 41 | 57 | 73 | 89 | 105 | 121 | 137 | 153 | 169 | 185 | 201 | 217 | 233 | 249 | 265 | 281 | 297 | 313 | 329 | 345 | 361 | 377 |
| J | 10 | 26 | 42 | 58 | 74 | 90 | 106 | 122 | 138 | 154 | 170 | 186 | 202 | 218 | 234 | 250 | 266 | 282 | 298 | 314 | 330 | 346 | 362 | 378 |
| K | 11 | 27 | 43 | 59 | 75 | 91 | 107 | 123 | 139 | 155 | 171 | 187 | 203 | 219 | 235 | 251 | 267 | 283 | 299 | 315 | 331 | 347 | 363 | 379 |
| L | 12 | 28 | 44 | 60 | 76 | 92 | 108 | 124 | 140 | 156 | 172 | 188 | 204 | 220 | 236 | 252 | 268 | 284 | 300 | 316 | 332 | 348 | 364 | 380 |
| M | 13 | 29 | 45 | 61 | 77 | 93 | 109 | 125 | 141 | 157 | 173 | 189 | 205 | 221 | 237 | 253 | 269 | 285 | 301 | 317 | 333 | 349 | 365 | 381 |
| N | 14 | 30 | 46 | 62 | 78 | 94 | 110 | 126 | 142 | 158 | 174 | 190 | 206 | 222 | 238 | 254 | 270 | 286 | 302 | 318 | 334 | 350 | 366 | 382 |
| O | 15 | 31 | 47 | 63 | 79 | 95 | 111 | 127 | 143 | 159 | 175 | 191 | 207 | 223 | 239 | 255 | 271 | 287 | 303 | 319 | 335 | 351 | 367 | 383 |
| P | 16 | 32 | 48 | 64 | 80 | 96 | 112 | 128 | 144 | 160 | 176 | 192 | 208 | 224 | 240 | 256 | 272 | 288 | 304 | 320 | 336 | 352 | 368 | 384 |

METHOD OF CONSTRUCTING SEQUENCING LIBRARY

CROSS-REFERENCE TO RELATED APPLICATIONS

The application is a continuation application of PCT Application No. PCT/CN2016/070789 filed on Jan. 13, 2016, which claims a priority to and benefits of Chinese Patent Application No. 201510058616.9, filed with the State Intellectual Property Office of P. R. China on Feb. 4, 2015, the entire contents of which are incorporated herein by reference.

FIELD

The present disclosure relates to the field of biotechnology, in particular to a method of constructing a sequencing library.

BACKGROUND

The next generation high-throughput sequencing technology based on massively parallel DNA sequencing platform has revolutionized genomic analysis, including the de novo assembly of whole genomes. Nevertheless, assembly of complex genomes remains challenging, in part due to the presence of dispersed repeats which introduces ambiguity during genome reconstruction, and to the presence of heterozygotic fragments derived from separate parental chromosomes which results in separate assembly of paired fragments from parental chromosomes after amplification.

By spanning highly repetitive regions and decreasing the assembly of homologous chromosomes, the combination of long-read sequences assembled by short-read sequences with isolation of haplotype can also help overcome problems posed by both repeats and heterozygosis. Recently, Illumina has produced TruSeq Synthetic Long-Read DNA library preparation kit to solve the problems caused by short-read sequences. However, because genomic DNA fragment is fragmented into a length of 8 to 10 kb in the initial step using such a DNA library preparation kit, the resulting DNA fragment is not long enough to overcome the deviations caused by large repeats, especially in a case of constructing a library of genome containing lots repeats. The application of Long Fragment Read Technology (LFR) developed by Complete Genomics is a case in point, which is able to construct a library with high accuracy using about 100 pg of human DNA per sample. Although LFR decreases the amount of genome in each well to 10% to 20% of a haploid genome using 384-well plate, the amount of genomic DNA fragment in each well is still not low enough to improve the efficiency of assembly.

Thus, there is a need in the field for an improved method of constructing a sequencing library to improve the accuracy and efficiency of the whole genome sequencing.

SUMMARY

Embodiments of the present disclosure seek to solve at least one of the problems existing in the related art to at least some extent.

The present disclosure develops a method of constructing a sequencing library of a long fragment in a length not less than 100 kb, using a genomic DNA fragment from a biology sample in an amount of 150 pg, in combination of multiple displacement amplification (MDA) and fragmentation by transposase, and based on nano-scale pipetting platform, so as to both optimize the procedure of library construction and improve the accuracy of library assembly.

In one aspect, the present disclosure provides in embodiments a method of constructing a sequencing library, comprising steps of 1) providing a single-stranded DNA fragment from a biological sample; 2) subjecting the single-stranded DNA fragment to whole genomic amplification to obtain a whole genome amplification product; 3) fragmenting the whole genome amplification product using a transposase embedded with two adaptors to obtain a fragmented product with two adaptors respectively at two ends; and 4) amplifying the fragmented product with two adaptors respectively at two ends using a tag sequence and a pair of primers to obtain said sequencing library.

In another aspect, the present disclosure provides in embodiments a method of constructing a sequencing library in a 5184-well plate, comprising 1) providing a single-stranded DNA fragment from a biological sample; 2) distributing the single-stranded DNA fragment to each well of the 5184-well plate, wherein the single-stranded DNA fragment in each well comprises 1% genome of the biological sample; 3) subjecting the single-stranded DNA fragment in each well of the 5184-well plate to whole genomic amplification to obtain a whole genome amplification product, wherein a reaction system in each well is in a volume less than 100 nL; 4) fragmenting the whole genome amplification product in each well of the 5184-well plate using a transposase embedded with two adaptors to obtain a fragmented product with two adaptors respectively at two ends; and 5) amplifying the fragmented product with two adaptors respectively at two ends in each well of the 5184-well plate using a tag sequence and a pair of primers to obtain said sequencing library, in which the tag sequence comprises a first tag sequence and a second tag sequence, in which the first tag sequence is composed of a third adaptor, a first random fragment and a first single-stranded DNA sequence in order from the 5' end to the 3' end and the second tag sequence is composed of a fourth adaptor, a second random fragment and a second single-stranded DNA sequence in order from the 5' end to the 3' end, and in which the first tag sequence comprises 72 tag sequences containing different said first random fragments respectively, and the second tag sequence comprises 72 tag sequences containing different said second random fragments respectively.

In still another aspect, the present disclosure provides in embodiments a packaged product customized for constructing a sequencing library in a length of 200 bp to 1100 bp, in which the packaged product comprises a 384-well plate, a 5184-well plate and a Nanodispenser, and each well of the 5184-well plate has a volume of 350 nL and an effective volume of 200 nL.

DETAILED DESCRIPTION

Figure 1:
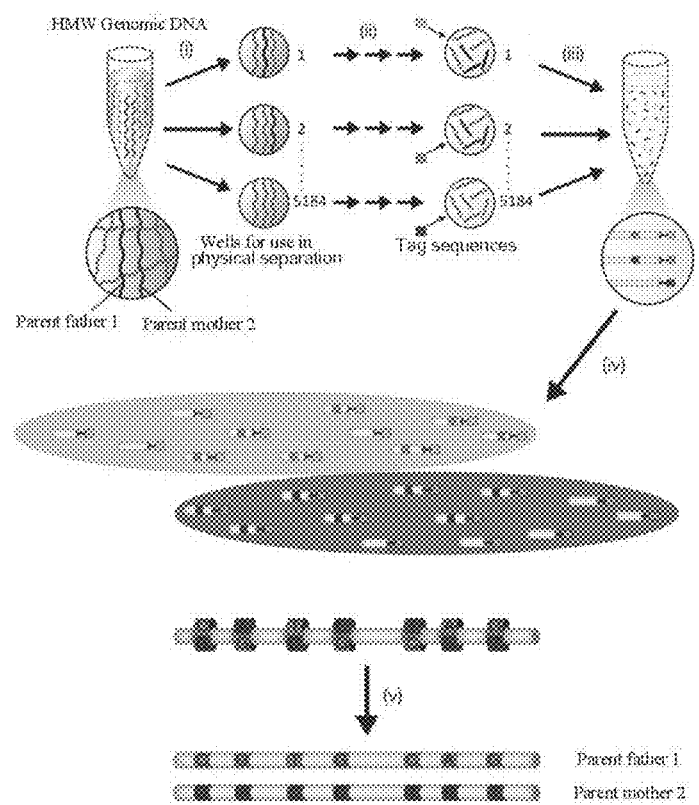
FIG. 1 is an overview showing a principle of sequencing according to embodiments of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

Terms used herein in the description of the present disclosure are only for the purpose of describing specific embodiments, but should not be construed to limit the present disclosure. As used in the description of the present disclosure and the appended claims, "a", "an" and "the" in singular forms mean including plural forms, unless clearly indicated in the context otherwise. It should also be understood that, as used herein, the term "and/or" represents and contains any one and all possible combinations of one or more associated listed items. It should be further understood that, when used in the specification, terms "comprising" and/or "containing" specify the presence of stated features, operations, elements and/or components, but do not exclude the presence or addition of one or more other features, operations, elements, components and/or groups thereof.

In addition, terms such as "first" and "second" are used herein for purposes of description and are not intended to indicate or imply relative importance or significance or impliedly indicate quantity of the technical feature referred to. Thus, the feature defined with "first" and "second" may comprise one or more this feature. In the description of the present disclosure, "a plurality of" means two or more than two this features, unless specified otherwise.

Figure 2:
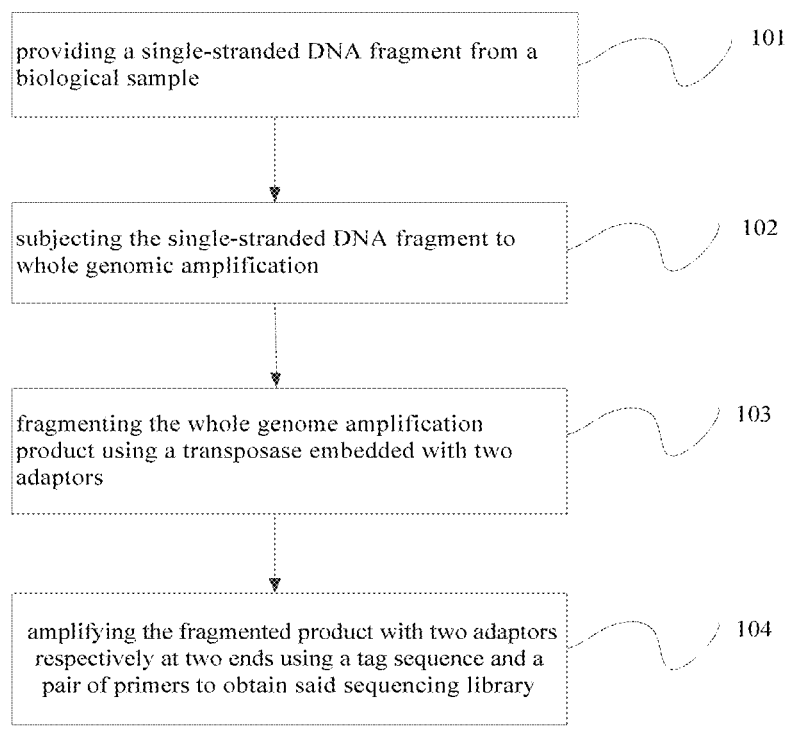
FIG. 2 is a flow chart showing a method of constructing a sequencing library according to an embodiment of the present disclosure.

In an aspect of the present disclosure, as shown in FIG. 2, provided is a method of constructing a sequencing library, comprising steps of S101: providing a single-stranded DNA fragment from a biological sample; S102: subjecting the single-stranded DNA fragment to whole genomic amplification to obtain a whole genome amplification product; S103: fragmenting the whole genome amplification product using a transposase embedded with two adaptors to obtain a fragmented product with two adaptors respectively at two ends; and S104: amplifying the fragmented product with two adaptors respectively at two ends using a tag sequence and a pair of primers to obtain said sequencing library.

Figure 3:
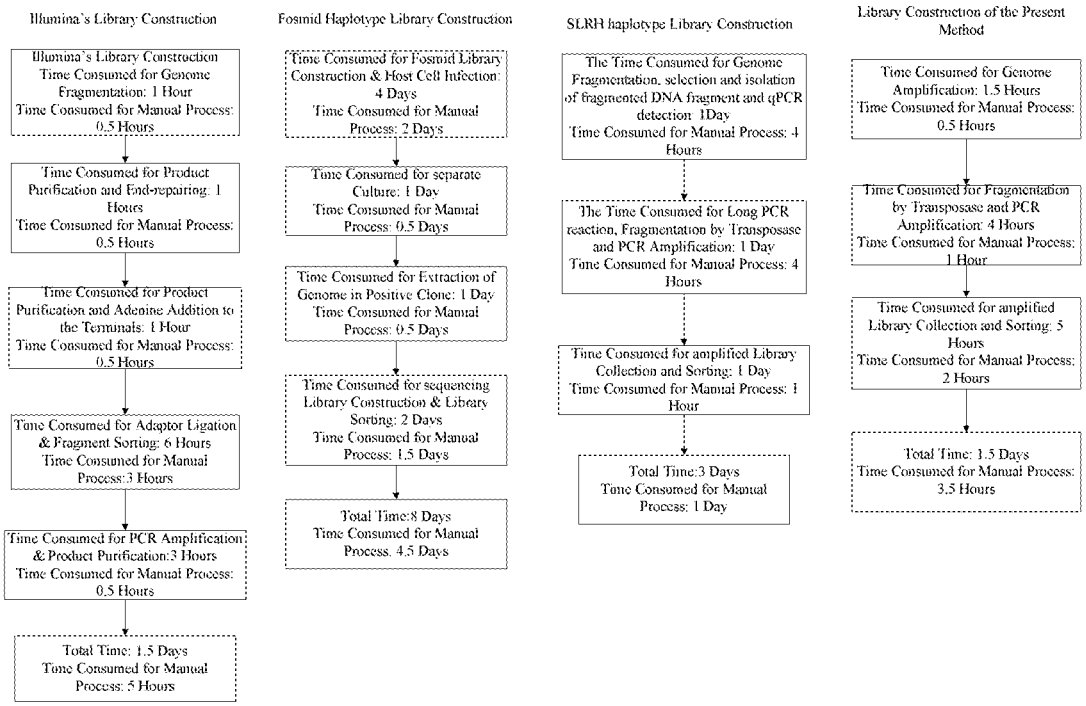
FIG. 3 is comparison of time consumed for a library construction method of the present method according to an embodiment of the present disclosure to that of the Illumina's library construction method, that of the Fosmid haplotype library construction method and that of the SLRH haplotype library construction method.
Figure 4:
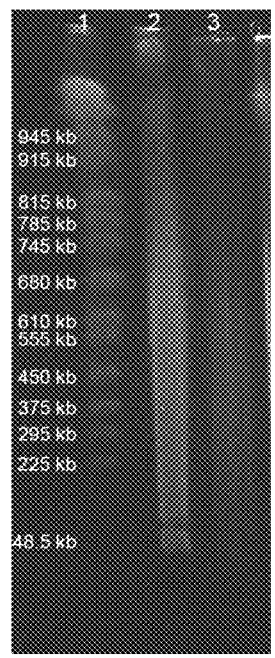
FIG. 4 is a schematic graph showing an electrophoresis result for genomic DNA fragment extracted according to the example 1 of the present disclosure.

Referring to FIG. 3, the Illumina's sequencing library is constructed by genome fragmentation, end-repairing the fragmented DNA fragment, adenine addition to the terminal, adaptor ligation, PCR amplification and product purification, and a total of 1.5 days is consumed for the library construction, in which a manual process takes 5 hours; the Fosmid haplotype library is constructed by host cell infection by expression vector, isolation and culture of the transformed host cell, extraction of genome in positive clone, sequencing library construction and library sorting, and a total of 8 days is consumed for the library construction, in which a manual process takes 4.5 days; the SLRH (statistically aided, long-read haplotyping) haplotype library is constructed by genome fragmentation, selection and isolation of fragmented DNA fragment and qPCR detection, and then Long PCR reaction, fragmentation by transposase and PCR amplification, finally amplified library collection and sorting, and a total of 3 days is consumed for the library construction, in which a manual process takes 1 day; while in embodiments of the present disclosure, a sequencing library is constructed by genome amplification, fragmentation by transposase, PCR amplification and amplified library collection and sorting, and a total of 1.5 days is consumed for the library construction, in which a manual process takes 3.5 hours. Thus, compared to the methods of library construction in the related art, the steps of library construction according to the present method is reduced, therefore shortening the total time consumed for the library construction and improving efficiency of the library construction.

S101: a single-stranded DNA fragment is provided from a biological sample.

In some embodiments of the present disclosure, the biological sample can be derived from at least one of plants, animals and microorganisms. In some embodiments of the present disclosure, the animal may be a mammal, such as human, *Drosophila*, zebrafish, mouse and the like; the plant may be *Arabidopsis thaliana*, rice and the like; the microorganism may be fungi and bacteria, such as *Escherichia coli*, yeast and the like. Preferably, the biological sample may be a human blood cell, more preferably, human leukocyte. Thus, a sequencing library of a long genomic DNA fragment in different species can be constructed efficiently.

In some embodiments of the present disclosure, the step of providing the single-stranded DNA fragment from the biological sample further comprises extracting a genomic DNA fragment from the biological sample, and subjecting the genomic DNA fragment to denaturation in an alkaline solution. The genomic DNA fragment has a length of 100 kb above, for example not less than 150 kb, not less than 200 kb, not less than 250 kb, not less than 300 kb, not less than 350 kb, not less than 400 kb, not less than 450 kb, not less than 500 kb, not less than 600 kb, not less than 700 kb, not less than 800 kb, not less than 900 kb, not less than 1000 kb, not less than 10 Mb, not less than 50 Mb, not less than 100 Mb, not less than 200 Mb, not less than 300 Mb, not less than 400 Mb, not less than 500 Mb, not less than 600 Mb, not less than 700 Mb, not less than 800 Mb, not less than 900 Mb, not less than 1000 Mb, not less than 1 Gb, not less than 2 Gb, not less than 3 Gb, not less than 4 Gb and the like, preferably 100 kb, more preferably 125 Mb, and most preferably 3 Gb. As to the existing method of constructing the sequencing library, the genomic DNA fragment is usually mechanically fragmented into small pieces on a sonicator such as Covaris LE220 sonicator, for example not greater than 1000 bp. In contrast, a genomic DNA fragment with a longer length can be provided by the present method, so as to improve the accuracy of the genome assembly by spanning the regions of repeats in genome.

Usually, a double-stranded DNA fragment was subjected to denaturation in an alkaline solution with a pH value, such as pH 12.6, by which the hydrogen bond in the double-stranded DNA fragment was broken, thus resulting in untied double helix structure, such that a single-stranded DNA fragment is obtained. In some embodiments of the present disclosure, the alkaline solution can be a potassium hydroxide solution, a sodium hydroxide solution, a calcium hydroxide solution, a sodium dodecyl sulfate (SDS) solution and the like, preferably the potassium hydroxide solution. In an embodiment of the present disclosure, the genomic DNA fragment is incubated in an alkaline solution at 20° C. to 30° C., for example 22° C., 23° C., 24° C., 25° C., 26° C., 27° C., 28° C., 29° C. and 30° C., preferably 25° C., for 1 to 3 minutes, for example 1 minute, 2 minutes, 3 minutes, preferably 2 minutes. In another embodiment of the present disclosure, the biological sample, such as a microorganism, is directly incubated in an alkaline solution at 80° C. to 90° C., for example 80° C., 81° C., 82° C., 83° C., 84° C., 85° C., 86° C., 87° C., 88° C., 89° C. and 90° C., preferably 85° C. for 1 to 3 minutes, for example 2 minutes, to obtain the single-stranded DNA fragment. Compared to extraction of the genomic DNA fragment in a physical or enzymological method, such as physical ultrasound or enzyme digestion, the alkali extraction process is utilized in the present disclosure, so as to ensure the extracted genomic DNA fragment in a length not less than 100 kb.

Human genome contains hyplotype information in a total amount of 6 GB. 150 pg of genomic DNA, extracted from 20 human cells, is used for the initial amount for reaction. Such an initial amount guarantees that a probability of homologous chromosome fragments derived from both mother and father at the same site in their respective genomes (i.e. such two homologous chromosome fragments are criss-cross) presenting in each physical separation (i.e. well) is less than 1%. The initial amount of the genomic DNA varies with different resources (species) of the biological sample to be test, with the initial amount of the genomic DNA extracted from 10 to 500 cells.

It is assumed that the cell number is "n", the number of the physical separations (i.e. wells) is "w", and the cell used contains diploid genome.

It is also defined that the amount of genome in each well is calculated by $\lambda=4n/w$.

It can be determined that the probability of homologous chromosome fragments derived from both mother and father at the same site in their respective genomes presenting in one same well satisfies the formula below:

$$P = \sum_{x=2}^{\infty} p(x), \ p(x) = \frac{e^{-\lambda} \cdot \lambda^x}{x!},$$

in which "x" represent a sequencing depth of a single base site.

Since the long fragments contained in each well deriving from mother and father are in a ratio of 1:1 (50% vs 50%), then the probability of the long fragments derived from both mother and father at the same site in their respective genomes is P*50%.

Accordingly, it can be determined based on the formula that the probability of homologous chromosome fragments derived from both mother and father at the same site in their respective genomes is related to the cell number and the number of the physical separations only, but irrelevant to a length of fragment added and a size of genome.

Figure 5:
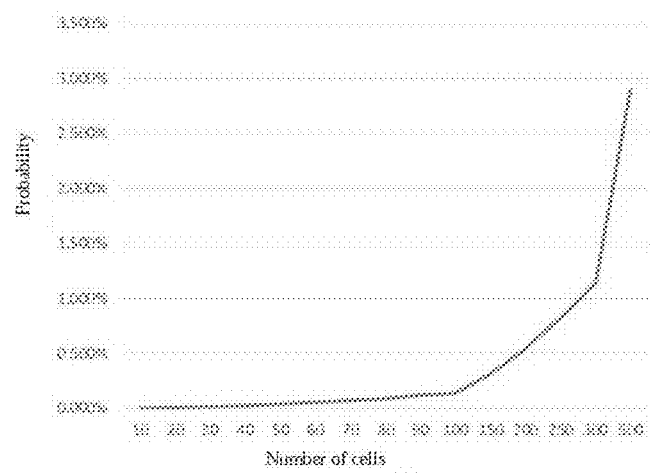
FIG. 5 is a schematic graph showing probability of homologous chromosomes in each well of a 5184-well plate as a function of the number of cells according to an exemplary embodiment of the present disclosure.

With the given number of physical separation, a distribution as shown in FIG. 5 is plotted by the cell number and the probability mentioned above, based on which the cell number for a certain probability can be calculated.

In order to meet the requirement that the probability of homologous chromosome fragments derived from both mother and father at the same site in their respective genomes is lower than 1%, the initial amount of the genomic DNA for all wells of the 5184-well plate is 10 to 500 cells.

In some embodiments of the present disclosure, as a staring material, a genomic DNA fragment of a biological sample is in an amount from 100 to 1000 pg. For example, the amount of the genomic DNA fragment is 100 pg, 150 pg, 250 pg, 300 pg, 350 pg, 400 pg, 450 pg, 500 pg, 600 pg, 700 pg, 800 pg, 900 pg or 1000 pg, preferably 150 pg, which is equivalent to about 25 human cells. Currently, the total amount of the genomic DNA fragment used to construct the Fosmid haplotype library is 8 μg, and the illumina Truseq synthetic long reads kit which is commercial available needs 500 ng genomic DNA fragment to construct a library. It is a significant advantage in the present disclosure to achieve a library construction just using 150 pg of the genomic DNA fragment as a staring material, so that the present method can be widely used to construct a library where a small amount of DNA fragment is present. For example, the method can be used to construct a haplotype library of free tumor cell, free fetal cell or embryonic cell in a trace amount. In addition, the use of trace amounts of DNA fragment as a starting material can significantly decrease the bias during multiple displacement amplification.

S102: the single-stranded DNA fragment is subjected to whole genomic amplification to obtain a whole genome amplification product.

To date, the whole genome amplification (WGA) comprises PCR amplification and isothermal amplification. The PCR amplification is selected from the group consisting of adaptor adapter PCR (LA-PCR), degenerate oligonucleotide-primed PCR (DOP-PCR) and primer-extension pre-amplification (PEP). The isothermal amplification is selected from the group consisting of Strand Displacement Amplification (SDA), multiple displacement amplification (MDA) and rolling circle amplification (RCA). In some embodiments of the present disclosure, the whole genome amplification is an isothermal amplification, preferably, multiple displacement amplification (MDA). In an embodiment, in the case that the biological sample is human genomic DNA, the single-stranded DNA fragment is incubated at 28° C. to 37° C., for example 30° C. for 45 to 75 minutes, for example 60 minutes. In another embodiment, in the case that the biological sample is microorganism, the single-stranded DNA fragment is incubated at 30° C. to 45°

C., for example 37° C. for 8 to 12 hours, for example 10 hours. In some embodiments, random primers used for MDA is in a length of 5 to 20 bp, for example 5 bp, 6 bp, 7 bp, 8 bp, 9 bp, 10 bp, 11 bp, 12 bp, 13 bp, 14 bp, 15 bp, 16 bp, 17 bp, 18 bp, 19 bp or 20 bp, preferably 8 bp. The reaction system in each well is in a volume less than 100 nL when using a 5184-well plate which is specific to the method of the present disclosure. Thus, a trace of DNA sample may be amplified by MDA to finally obtain a large amount of high quality DNA fragments with high molecular weight, with a low level of amplification bias and mutation accumulation.

In some embodiments of the present disclosure, the multiple displacement amplification of the single-stranded DNA fragment in the present disclosure further comprises incubating the amplified product to 65° C. for 5 minutes to stop the amplification.

S103: the whole genome amplification product is fragmented using a transposase embedded with two adaptors, to obtain a fragmented product with two adaptors respectively at two ends.

In some embodiments of the present disclosure, the transposase is embedded with a first adaptor and a second adaptor, and the first adaptor is of a sequence different from that of the second sequence. The first adaptor comprises a first long-chain sequence and a first short-chain sequence, and the first long-chain sequence is composed of a region unpaired with the first short-chain sequence and a region paired with the first short-chain sequence in order from the 5' end to the 3' end. The second adaptor comprises a second long-chain sequence and a second short-chain sequence, and the second long-chain sequence is composed of a region unpaired with the second short-chain sequence and a region paired with the second short-chain sequence in order from the 5' end to the 3' end.

The first adaptor and the second adaptor in the examples of the present disclosure are designed for the illumina's sequencing platform, and their sequences are listed as follows:

TABLE 1

Sequences of the first adaptor and the second adaptor

| Name | Sequence |
|---|---|
| the first adaptor | 5'-GTCTCGTGGGCTCGGAGATGTGTATAAGAGACAG-3' (SEQ ID NO. 145)<br>3'-TCTACACATATTCTCTGTC-5' (SEQ ID NO. 146) |
| the second adaptor | 5'-TCGTCGGCAGCGTCAGATGTGTATAAGAGACAG-3' (SEQ ID NO. 147)<br>3'-TCTACACATATTCTCTGTC-5' (SEQ ID NO. 148) |

The sequences of the first adaptor and the second adaptor can vary depending on the types of sequencing platforms, which are designed according to the following principles:

1. The first adaptor comprises a first long-chain sequence and a first short-chain sequence, and the second adaptor comprises a second long-chain sequence and a second short-chain sequence;

2. The long-chain sequences of the first and second adaptors each contains a fixed sequence of AGATGTG-TATAAGAGACAG (in order of the 5' end to the 3' end, and in a length of 19 bp) at the 3' end of the long-chain sequence;

3. The region unpaired with the short-chain sequence of the long-chain sequence can vary depending on the types of sequencing platforms, for example, for the IonProton™ sequencer of Life Technology, the first long-chain of the first adaptor has a sequence of 5'-CCTCTCTATGGGCAGTCG-GTGATAGATGTGTATAAGAGACAG-3', and the second long-chain of the second adaptor has a sequence of 5'-CCATCTCATCCCTGCGTGTCTCCGACTCAGAGAT-GTGTATAAGAGACAG-3';

4. The short-chain sequences of the first and second adaptors each contains a fixed sequence of 3'-TCTACACAT-ATTCTCTGTC-5' (in a length of 19 bp) which is complementary paired with the above fixed sequence at the 3' end of the long-chain sequence.

5. The sequence of the first adaptor is same or different to that of the second adaptor, preferably the sequence of the first adaptor is different to that of the second adaptor.

In some embodiments of the present disclosure, the whole genome amplification product is incubated in a reaction system containing a transposase embedded with a first adaptor and a second adaptor at 50° C. to 60° C. for 5 to 20 minutes, preferably incubated at 55° C. for 10 minutes. The step of fragmentation further comprises applying a transesterase stop buffer to the reaction mixture after completion of the incubation to stop the fragmentation, thereby obtaining a fragmented product with two adaptors respectively at two ends which is in a length of 300 bp to 1000 bp, for example, 300 bp, 400 bp, 500 bp, 600 bp, 700 bp, 800 bp, 900 bp or 1000 bp.

S104: the fragmented product with two adaptors respectively at two ends is amplified using a tag sequence and a pair of primers to obtain said sequencing library.

In some embodiments of the present disclosure, the tag sequence comprises a first tag sequence and a second tag sequence. The first tag sequence is composed of a third adaptor (for subsequent sequencing), a first random fragment (serving as a first tag) and a first single-stranded DNA sequence in order from the 5' end to the 3' end, and the second tag sequence is composed of a fourth adaptor (for subsequent sequencing), a second random fragment (serving as a second tag) and a second single-stranded DNA sequence in order from the 5' end to the 3' end. The first single-stranded DNA sequence is identical to the region unpaired with the first short-chain sequence of the first adaptor, and the second single-stranded DNA sequence is identical to the region unpaired with the second short-chain sequence of the second adaptor. The first tag sequence comprises 72 first tag sequences containing different said first random fragments respectively, and the second tag sequence comprises 72 second tag sequences containing different said second random fragments respectively. The first random fragment and the second random fragment each have a length of 5 bp to 20 bp, for example, 5 bp, 6 bp, 7 bp, 8 bp, 9 bp, 10 bp, 11 bp, 12 bp, 13 bp, 14 bp, 15 bp, 16 bp, 17 bp, 18 bp, 19 bp or 20 bp, preferably 8 bp. The sequences of the third adaptor and the fourth adaptor vary depending to the types of sequencing platforms. The first tag sequence in the examples of the present disclosure is shown in Table 2. The second tag sequence in the examples of the present disclosure is shown in Table 3.

TABLE 2

Sequences of the 72 first tag sequences

| NO. | Sequence from the 5' end to the 3' end | sequence number |
|---|---|---|
| N701 | CAAGCAGAAGACGGCATACGAGATTCGCCTTAGTCTCGTGGGCTCGG | SEQ ID NO.: 1 |
| N702 | CAAGCAGAAGACGGCATACGAGATCTAGTACGGTCTCGTGGGCTCGG | SEQ ID NO.: 2 |
| N703 | CAAGCAGAAGACGGCATACGAGATTTCTGCCTGTCTCGTGGGCTCGG | SEQ ID NO.: 3 |
| N704 | CAAGCAGAAGACGGCATACGAGATGCTCAGGAGTCTCGTGGGCTCGG | SEQ ID NO.: 4 |
| N705 | CAAGCAGAAGACGGCATACGAGATAGGAGTCCGTCTCGTGGGCTCGG | SEQ ID NO.: 5 |
| N706 | CAAGCAGAAGACGGCATACGAGATCATGCCTAGTCTCGTGGGCTCGG | SEQ ID NO.: 6 |
| N707 | CAAGCAGAAGACGGCATACGAGATGTAGAGAGGTCTCGTGGGCTCGG | SEQ ID NO.: 7 |
| N708 | CAAGCAGAAGACGGCATACGAGATCCTCTCTGGTCTCGTGGGCTCGG | SEQ ID NO.: 8 |
| N709 | CAAGCAGAAGACGGCATACGAGATAGCGTAGCGTCTCGTGGGCTCGG | SEQ ID NO.: 9 |
| N710 | CAAGCAGAAGACGGCATACGAGATCAGCCTCGGTCTCGTGGGCTCGG | SEQ ID NO.: 10 |
| N711 | CAAGCAGAAGACGGCATACGAGATTGCCTCTTGTCTCGTGGGCTCGG | SEQ ID NO.: 11 |
| N712 | CAAGCAGAAGACGGCATACGAGATTCCTCTACGTCTCGTGGGCTCGG | SEQ ID NO.: 12 |
| N713 | CAAGCAGAAGACGGCATACGAGATAAGCAATGGTCTCGTGGGCTCGG | SEQ ID NO.: 13 |
| N714 | CAAGCAGAAGACGGCATACGAGATAATCCGAAGTCTCGTGGGCTCGG | SEQ ID NO.: 14 |
| N715 | CAAGCAGAAGACGGCATACGAGATAATGATGAGTCTCGTGGGCTCGG | SEQ ID NO.: 15 |
| N716 | CAAGCAGAAGACGGCATACGAGATACAGGAGCGTCTCGTGGGCTCGG | SEQ ID NO.: 16 |
| N717 | CAAGCAGAAGACGGCATACGAGATACCGAGCTGTCTCGTGGGCTCGG | SEQ ID NO.: 17 |
| N718 | CAAGCAGAAGACGGCATACGAGATACCTGTTGGTCTCGTGGGCTCGG | SEQ ID NO.: 18 |
| N719 | CAAGCAGAAGACGGCATACGAGATACCTTGAAGTCTCGTGGGCTCGG | SEQ ID NO.: 19 |
| N720 | CAAGCAGAAGACGGCATACGAGATACTACGTGGTCTCGTGGGCTCGG | SEQ ID NO.: 20 |
| N721 | CAAGCAGAAGACGGCATACGAGATACTCTTACGTCTCGTGGGCTCGG | SEQ ID NO.: 21 |
| N722 | CAAGCAGAAGACGGCATACGAGATAGAAGGTAGTCTCGTGGGCTCGG | SEQ ID NO.: 22 |
| N723 | CAAGCAGAAGACGGCATACGAGATAGAGACTTGTCTCGTGGGCTCGG | SEQ ID NO.: 23 |
| N724 | CAAGCAGAAGACGGCATACGAGATAGATCTCTGTCTCGTGGGCTCGG | SEQ ID NO.: 24 |
| N725 | CAAGCAGAAGACGGCATACGAGATAGGTTCATGTCTCGTGGGCTCGG | SEQ ID NO.: 25 |
| N726 | CAAGCAGAAGACGGCATACGAGATAGTCTGGTGTCTCGTGGGCTCGG | SEQ ID NO.: 26 |
| N727 | CAAGCAGAAGACGGCATACGAGATAGTTATAGGTCTCGTGGGCTCGG | SEQ ID NO.: 27 |
| N728 | CAAGCAGAAGACGGCATACGAGATAGTTCCGCGTCTCGTGGGCTCGG | SEQ ID NO.: 28 |
| N729 | CAAGCAGAAGACGGCATACGAGATATAACTAGGTCTCGTGGGCTCGG | SEQ ID NO.: 29 |
| N730 | CAAGCAGAAGACGGCATACGAGATATATAAGAGTCTCGTGGGCTCGG | SEQ ID NO.: 30 |
| N731 | CAAGCAGAAGACGGCATACGAGATATCGATTCGTCTCGTGGGCTCGG | SEQ ID NO.: 31 |
| N732 | CAAGCAGAAGACGGCATACGAGATATCTTATTGTCTCGTGGGCTCGG | SEQ ID NO.: 32 |
| N733 | CAAGCAGAAGACGGCATACGAGATATGGCATAGTCTCGTGGGCTCGG | SEQ ID NO.: 33 |
| N734 | CAAGCAGAAGACGGCATACGAGATATTAGAATGTCTCGTGGGCTCGG | SEQ ID NO.: 34 |
| N735 | CAAGCAGAAGACGGCATACGAGATCAACATTAGTCTCGTGGGCTCGG | SEQ ID NO.: 35 |
| N736 | CAAGCAGAAGACGGCATACGAGATCAAGTAACGTCTCGTGGGCTCGG | SEQ ID NO.: 36 |
| N737 | CAAGCAGAAGACGGCATACGAGATCAGTGAATGTCTCGTGGGCTCGG | SEQ ID NO.: 37 |
| N738 | CAAGCAGAAGACGGCATACGAGATCATATGATGTCTCGTGGGCTCGG | SEQ ID NO.: 38 |

TABLE 2-continued

Sequences of the 72 first tag sequences

| NO. | Sequence from the 5' end to the 3' end | sequence number |
|---|---|---|
| N739 | CAAGCAGAAGACGGCATACGAGAT*CATTAAGC*GTCTCGTGGGCTCGG | SEQ ID NO.: 39 |
| N740 | CAAGCAGAAGACGGCATACGAGAT*CCATATCC*GTCTCGTGGGCTCGG | SEQ ID NO.: 40 |
| N741 | CAAGCAGAAGACGGCATACGAGAT*CCATCAAG*GTCTCGTGGGCTCGG | SEQ ID NO.: 41 |
| N742 | CAAGCAGAAGACGGCATACGAGAT*CCGATCTT*GTCTCGTGGGCTCGG | SEQ ID NO.: 42 |
| N743 | CAAGCAGAAGACGGCATACGAGAT*CCGGTTAA*GTCTCGTGGGCTCGG | SEQ ID NO.: 43 |
| N744 | CAAGCAGAAGACGGCATACGAGAT*CGACTTAG*GTCTCGTGGGCTCGG | SEQ ID NO.: 44 |
| N745 | CAAGCAGAAGACGGCATACGAGAT*CGCGAATA*GTCTCGTGGGCTCGG | SEQ ID NO.: 45 |
| N746 | CAAGCAGAAGACGGCATACGAGAT*CGTGCTTC*GTCTCGTGGGCTCGG | SEQ ID NO.: 46 |
| N747 | CAAGCAGAAGACGGCATACGAGAT*CTACTGGA*GTCTCGTGGGCTCGG | SEQ ID NO.: 47 |
| N748 | CAAGCAGAAGACGGCATACGAGAT*CTAGACAA*GTCTCGTGGGCTCGG | SEQ ID NO.: 48 |
| N749 | CAAGCAGAAGACGGCATACGAGAT*TGTCGAAC*GTCTCGTGGGCTCGG | SEQ ID NO.: 49 |
| N750 | CAAGCAGAAGACGGCATACGAGAT*CGATAGAT*GTCTCGTGGGCTCGG | SEQ ID NO.: 50 |
| N751 | CAAGCAGAAGACGGCATACGAGAT*AACAGTAA*GTCTCGTGGGCTCGG | SEQ ID NO.: 51 |
| N752 | CAAGCAGAAGACGGCATACGAGAT*CCGCGTGT*GTCTCGTGGGCTCGG | SEQ ID NO.: 52 |
| N753 | CAAGCAGAAGACGGCATACGAGAT*TCTGGATA*GTCTCGTGGGCTCGG | SEQ ID NO.: 53 |
| N754 | CAAGCAGAAGACGGCATACGAGAT*TATTCCTA*GTCTCGTGGGCTCGG | SEQ ID NO.: 54 |
| N755 | CAAGCAGAAGACGGCATACGAGAT*TCACGTTC*GTCTCGTGGGCTCGG | SEQ ID NO.: 55 |
| N756 | CAAGCAGAAGACGGCATACGAGAT*AACGCAAT*GTCTCGTGGGCTCGG | SEQ ID NO.: 56 |
| N757 | CAAGCAGAAGACGGCATACGAGAT*GCTTACGA*GTCTCGTGGGCTCGG | SEQ ID NO.: 57 |
| N758 | CAAGCAGAAGACGGCATACGAGAT*TACTTCGC*GTCTCGTGGGCTCGG | SEQ ID NO.: 58 |
| N759 | CAAGCAGAAGACGGCATACGAGAT*CGCAGTCC*GTCTCGTGGGCTCGG | SEQ ID NO.: 59 |
| N760 | CAAGCAGAAGACGGCATACGAGAT*CAATGCTC*GTCTCGTGGGCTCGG | SEQ ID NO.: 60 |
| N761 | CAAGCAGAAGACGGCATACGAGAT*CACGGCGA*GTCTCGTGGGCTCGG | SEQ ID NO.: 61 |
| N762 | CAAGCAGAAGACGGCATACGAGAT*CGCCGCTG*GTCTCGTGGGCTCGG | SEQ ID NO.: 62 |
| N763 | CAAGCAGAAGACGGCATACGAGAT*GCATCCTT*GTCTCGTGGGCTCGG | SEQ ID NO.: 63 |
| N764 | CAAGCAGAAGACGGCATACGAGAT*GCCATTGC*GTCTCGTGGGCTCGG | SEQ ID NO.: 64 |
| N765 | CAAGCAGAAGACGGCATACGAGAT*GAGAATAC*GTCTCGTGGGCTCGG | SEQ ID NO.: 65 |
| N766 | CAAGCAGAAGACGGCATACGAGAT*GTAATGAC*GTCTCGTGGGCTCGG | SEQ ID NO.: 66 |
| N767 | CAAGCAGAAGACGGCATACGAGAT*GCTTGGAT*GTCTCGTGGGCTCGG | SEQ ID NO.: 67 |
| N768 | CAAGCAGAAGACGGCATACGAGAT*AGTATACC*GTCTCGTGGGCTCGG | SEQ ID NO.: 68 |
| N769 | CAAGCAGAAGACGGCATACGAGAT*GCACGCAA*GTCTCGTGGGCTCGG | SEQ ID NO.: 69 |
| N770 | CAAGCAGAAGACGGCATACGAGAT*CCGTCGGA*GTCTCGTGGGCTCGG | SEQ ID NO.: 70 |
| N771 | CAAGCAGAAGACGGCATACGAGAT*ATGCCTGC*GTCTCGTGGGCTCGG | SEQ ID NO.: 71 |
| N772 | CAAGCAGAAGACGGCATACGAGAT*TCGCTGGC*GTCTCGTGGGCTCGG | SEQ ID NO.: 72 |

It should be noted in Table 2 that the sequence of the third adaptor is underlined, the first random fragment composed of 8 bases is in the italic type, and the first single-stranded DNA sequence is in the bold font, in which the first single-stranded DNA sequence is identical to the region unpaired with the first short-chain sequence of the first long-chain sequence in the first adaptor.

TABLE 3

Sequences of the 72 second tag sequences

| NO. | Sequence from the 5' end to the 3' end | sequence number |
|---|---|---|
| N501 | AATGATACGGCGACCACCGAGATCTACAC*TAGATCGC*TCGTCGGCAGCGTC | SEQ ID NO.: 73 |
| N502 | AATGATACGGCGACCACCGAGATCTACAC*CTCTCTAT*TCGTCGGCAGCGTC | SEQ ID NO.: 74 |
| N503 | AATGATACGGCGACCACCGAGATCTACAC*TATCCTCT*TCGTCGGCAGCGTC | SEQ ID NO.: 75 |
| N504 | AATGATACGGCGACCACCGAGATCTACAC*AGAGTAGA*TCGTCGGCAGCGTC | SEQ ID NO.: 76 |
| N505 | AATGATACGGCGACCACCGAGATCTACAC*GTAAGGAG*TCGTCGGCAGCGTC | SEQ ID NO.: 77 |
| N506 | AATGATACGGCGACCACCGAGATCTACAC*ACTGCATA*TCGTCGGCAGCGTC | SEQ ID NO.: 78 |
| N507 | AATGATACGGCGACCACCGAGATCTACAC*AAGGAGTA*TCGTCGGCAGCGTC | SEQ ID NO.: 79 |
| N508 | AATGATACGGCGACCACCGAGATCTACAC*CTAAGCCT*TCGTCGGCAGCGTC | SEQ ID NO.: 80 |
| N509 | AATGATACGGCGACCACCGAGATCTACAC*CTAGCGCT*TCGTCGGCAGCGTC | SEQ ID NO.: 81 |
| N510 | AATGATACGGCGACCACCGAGATCTACAC*CTCACAGG*TCGTCGGCAGCGTC | SEQ ID NO.: 82 |
| N511 | AATGATACGGCGACCACCGAGATCTACAC*CTTAGTTG*TCGTCGGCAGCGTC | SEQ ID NO.: 83 |
| N512 | AATGATACGGCGACCACCGAGATCTACAC*CTTCCTAT*TCGTCGGCAGCGTC | SEQ ID NO.: 84 |
| N513 | AATGATACGGCGACCACCGAGATCTACAC*CTTGTAGT*TCGTCGGCAGCGTC | SEQ ID NO.: 85 |
| N514 | AATGATACGGCGACCACCGAGATCTACAC*GAACCATC*TCGTCGGCAGCGTC | SEQ ID NO.: 86 |
| N515 | AATGATACGGCGACCACCGAGATCTACAC*GAATGTGG*TCGTCGGCAGCGTC | SEQ ID NO.: 87 |
| N516 | AATGATACGGCGACCACCGAGATCTACAC*GACCAAGA*TCGTCGGCAGCGTC | SEQ ID NO.: 88 |
| N517 | AATGATACGGCGACCACCGAGATCTACAC*GATCCTCG*TCGTCGGCAGCGTC | SEQ ID NO.: 89 |
| N518 | AATGATACGGCGACCACCGAGATCTACAC*GATGGACT*TCGTCGGCAGCGTC | SEQ ID NO.: 90 |
| N519 | AATGATACGGCGACCACCGAGATCTACAC*GATTAGTG*TCGTCGGCAGCGTC | SEQ ID NO.: 91 |
| N520 | AATGATACGGCGACCACCGAGATCTACAC*GCGCCTTA*TCGTCGGCAGCGTC | SEQ ID NO.: 92 |
| N521 | AATGATACGGCGACCACCGAGATCTACAC*GGAACAGT*TCGTCGGCAGCGTC | SEQ ID NO.: 93 |
| N522 | AATGATACGGCGACCACCGAGATCTACAC*GGAGGAAG*TCGTCGGCAGCGTC | SEQ ID NO.: 94 |
| N523 | AATGATACGGCGACCACCGAGATCTACAC*GGAGTCGC*TCGTCGGCAGCGTC | SEQ ID NO.: 95 |
| N524 | AATGATACGGCGACCACCGAGATCTACAC*GGCCTGTA*TCGTCGGCAGCGTC | SEQ ID NO.: 96 |
| N525 | AATGATACGGCGACCACCGAGATCTACAC*GGCTTAAC*TCGTCGGCAGCGTC | SEQ ID NO.: 97 |
| N526 | AATGATACGGCGACCACCGAGATCTACAC*GGTAATTA*TCGTCGGCAGCGTC | SEQ ID NO.: 98 |
| N527 | AATGATACGGCGACCACCGAGATCTACAC*GGTGTTAT*TCGTCGGCAGCGTC | SEQ ID NO.: 99 |
| N528 | AATGATACGGCGACCACCGAGATCTACAC*GTCCTACG*TCGTCGGCAGCGTC | SEQ ID NO.: 100 |
| N529 | AATGATACGGCGACCACCGAGATCTACAC*GTCGAGAG*TCGTCGGCAGCGTC | SEQ ID NO.: 101 |
| N530 | AATGATACGGCGACCACCGAGATCTACAC*GTGCGTAG*TCGTCGGCAGCGTC | SEQ ID NO.: 102 |
| N531 | AATGATACGGCGACCACCGAGATCTACAC*GTTAACCT*TCGTCGGCAGCGTC | SEQ ID NO.: 103 |
| N532 | AATGATACGGCGACCACCGAGATCTACAC*GTTGCAAC*TCGTCGGCAGCGTC | SEQ ID NO.: 104 |
| N533 | AATGATACGGCGACCACCGAGATCTACAC*TAATTGAG*TCGTCGGCAGCGTC | SEQ ID NO.: 105 |
| N534 | AATGATACGGCGACCACCGAGATCTACAC*TAGACTTG*TCGTCGGCAGCGTC | SEQ ID NO.: 106 |
| N535 | AATGATACGGCGACCACCGAGATCTACAC*TAGGTTGT*TCGTCGGCAGCGTC | SEQ ID NO.: 107 |
| N536 | AATGATACGGCGACCACCGAGATCTACAC*TATGGTAG*TCGTCGGCAGCGTC | SEQ ID NO.: 108 |
| N537 | AATGATACGGCGACCACCGAGATCTACAC*TATGTGTC*TCGTCGGCAGCGTC | SEQ ID NO.: 109 |
| N538 | AATGATACGGCGACCACCGAGATCTACAC*TATTATCT*TCGTCGGCAGCGTC | SEQ ID NO.: 110 |

TABLE 3-continued

Sequences of the 72 second tag sequences

| NO. | Sequence from the 5' end to the 3' end | sequence number |
|---|---|---|
| N539 | <u>AATGATACGGCGACCACCGAGATCTACAC</u>*TCACCGCG*TCGTCGGCAGCGTC | SEQ ID NO.: 111 |
| N540 | <u>AATGATACGGCGACCACCGAGATCTACAC</u>*TCATAGTA*TCGTCGGCAGCGTC | SEQ ID NO.: 112 |
| N541 | <u>AATGATACGGCGACCACCGAGATCTACAC</u>*TCCAACAA*TCGTCGGCAGCGTC | SEQ ID NO.: 113 |
| N542 | <u>AATGATACGGCGACCACCGAGATCTACAC</u>*TCCTCACT*TCGTCGGCAGCGTC | SEQ ID NO.: 114 |
| N543 | <u>AATGATACGGCGACCACCGAGATCTACAC</u>*TCGGCGAT*TCGTCGGCAGCGTC | SEQ ID NO.: 115 |
| N544 | <u>AATGATACGGCGACCACCGAGATCTACAC</u>*TCTATAAG*TCGTCGGCAGCGTC | SEQ ID NO.: 116 |
| N545 | <u>AATGATACGGCGACCACCGAGATCTACAC</u>*TCTCATGG*TCGTCGGCAGCGTC | SEQ ID NO.: 117 |
| N546 | <u>AATGATACGGCGACCACCGAGATCTACAC</u>*TGAGGTGA*TCGTCGGCAGCGTC | SEQ ID NO.: 118 |
| N547 | <u>AATGATACGGCGACCACCGAGATCTACAC</u>*TGCAAGGT*TCGTCGGCAGCGTC | SEQ ID NO.: 119 |
| N548 | <u>AATGATACGGCGACCACCGAGATCTACAC</u>*TGGAGTAT*TCGTCGGCAGCGTC | SEQ ID NO.: 120 |
| N549 | <u>AATGATACGGCGACCACCGAGATCTACAC</u>*GCGAGGCC*TCGTCGGCAGCGTC | SEQ ID NO.: 121 |
| N550 | <u>AATGATACGGCGACCACCGAGATCTACAC</u>*TGCGCGCC*TCGTCGGCAGCGTC | SEQ ID NO.: 122 |
| N551 | <u>AATGATACGGCGACCACCGAGATCTACAC</u>*AGGTGGCG*TCGTCGGCAGCGTC | SEQ ID NO.: 123 |
| N552 | <u>AATGATACGGCGACCACCGAGATCTACAC</u>*GCCGCATG*TCGTCGGCAGCGTC | SEQ ID NO.: 124 |
| N553 | <u>AATGATACGGCGACCACCGAGATCTACAC</u>*CTGTTGCC*TCGTCGGCAGCGTC | SEQ ID NO.: 125 |
| N554 | <u>AATGATACGGCGACCACCGAGATCTACAC</u>*TGATACCG*TCGTCGGCAGCGTC | SEQ ID NO.: 126 |
| N555 | <u>AATGATACGGCGACCACCGAGATCTACAC</u>*ATTGGCCG*TCGTCGGCAGCGTC | SEQ ID NO.: 127 |
| N556 | <u>AATGATACGGCGACCACCGAGATCTACAC</u>*GGACGGCT*TCGTCGGCAGCGTC | SEQ ID NO.: 128 |
| N557 | <u>AATGATACGGCGACCACCGAGATCTACAC</u>*CACTCTGT*TCGTCGGCAGCGTC | SEQ ID NO.: 129 |
| N558 | <u>AATGATACGGCGACCACCGAGATCTACAC</u>*GGCTGCGT*TCGTCGGCAGCGTC | SEQ ID NO.: 130 |
| N559 | <u>AATGATACGGCGACCACCGAGATCTACAC</u>*GTCAGCTC*TCGTCGGCAGCGTC | SEQ ID NO.: 131 |
| N560 | <u>AATGATACGGCGACCACCGAGATCTACAC</u>*AGCCATCA*TCGTCGGCAGCGTC | SEQ ID NO.: 132 |
| N561 | <u>AATGATACGGCGACCACCGAGATCTACAC</u>*ATGATTCA*TCGTCGGCAGCGTC | SEQ ID NO.: 133 |
| N562 | <u>AATGATACGGCGACCACCGAGATCTACAC</u>*GTCTGTCA*TCGTCGGCAGCGTC | SEQ ID NO.: 134 |
| N563 | <u>AATGATACGGCGACCACCGAGATCTACAC</u>*CGACCACT*TCGTCGGCAGCGTC | SEQ ID NO.: 135 |
| N564 | <u>AATGATACGGCGACCACCGAGATCTACAC</u>*CTCCACGC*TCGTCGGCAGCGTC | SEQ ID NO.: 136 |
| N565 | <u>AATGATACGGCGACCACCGAGATCTACAC</u>*GCGGAAGT*TCGTCGGCAGCGTC | SEQ ID NO.: 137 |
| N566 | <u>AATGATACGGCGACCACCGAGATCTACAC</u>*GTACATGT*TCGTCGGCAGCGTC | SEQ ID NO.: 138 |
| N567 | <u>AATGATACGGCGACCACCGAGATCTACAC</u>*TTAGCCGG*TCGTCGGCAGCGTC | SEQ ID NO.: 139 |
| N568 | <u>AATGATACGGCGACCACCGAGATCTACAC</u>*CAGGATCG*TCGTCGGCAGCGTC | SEQ ID NO.: 140 |
| N569 | <u>AATGATACGGCGACCACCGAGATCTACAC</u>*ATATCGTC*TCGTCGGCAGCGTC | SEQ ID NO.: 141 |
| N570 | <u>AATGATACGGCGACCACCGAGATCTACAC</u>*TGGCCAGG*TCGTCGGCAGCGTC | SEQ ID NO.: 142 |
| N571 | <u>AATGATACGGCGACCACCGAGATCTACAC</u>*TAGAGAGC*TCGTCGGCAGCGTC | SEQ ID NO.: 143 |
| N572 | <u>AATGATACGGCGACCACCGAGATCTACAC</u>*GACACGCT*TCGTCGGCAGCGTC | SEQ ID NO.: 144 |

It should be noted in Table 3 that the sequence of the fourth adaptor is underlined, the second random fragment composed of 8 bases is in the italic type, and the second single-stranded DNA sequence is in the bold font, in which the second single-stranded DNA sequence is identical to the region unpaired with the second short-chain sequence of the second long-chain sequence in the second adaptor.

In some embodiments of the present disclosure, the pair of primers comprises a first primer and a second primer. The first primer is of a sequence identical or complementary to part of the sequence of the third adaptor, and the second primer is of a sequence identical or complementary to part of the sequence of the fourth adaptor. The sequences of the first primer and the second primer (in the case that the first primer is identical to the third adaptor, and the second primer is identical to the fourth adaptor) are shown in Table 4.

TABLE 4

Sequences of the first primer and the second primer

| Name | Sequence of the 5' end to the 3' end |
|---|---|
| the first primer | CAAGCAGAAGACGGCATACGA (SEQ ID NO. 149); or GTTCGTCTTCTGCCGTATGCT (SEQ ID NO. 151) |
| the second primer | AATGATACGGCGACCACCGA (SEQ ID NO. 150); or TTACTATGCCGCTGGTGGCT (SEQ ID NO. 152) |

In some embodiments of the present disclosure, the fragmented product with two adaptors respectively at two ends is subjected to polymerase chain reaction using the first tag sequence and the second tag sequence as well as the first primer and the second primer, thus obtaining the sequencing library of the present disclosure.

In some embodiments of the present disclosure, the sequencing library of the present disclosure is purified by magnetic beads or agarose gel electrophoresis, thus obtaining a purified sequencing library in a length of 200 bp to 1100 bp, for example, 200 bp, 300 bp, 400 bp, 500 bp, 600 bp, 700 bp, 800 bp, 900 bp, 1000 bp or 1100 bp. The sequencing library of the present disclosure is optionally sorted using magnetic beads mixed with the library in a proportion or agarose gel electrophoresis, for example using magnetic beads mixed with the library in equal ratios or 0.2% of agarose gel electrophoresis.

In some embodiments of the present disclosure, the steps of 2) to 4), also referred to step 102 to step 104 are carried out in a 5184-well plate. According to a predetermined procedure, the reaction solution is equally distributed into wells of a 384-well plate by a multichannel pipette, and then the reaction solution in the wells of 384-well plate is equally distributed into wells of a 5184-well plate by Multisample Nanodispenser (WaferGen).

In further another aspect of the present disclosure, provided is a 5184-well plate which is specific to the method of the present disclosure. The 5184-well plate of the present disclosure has a volume of 350 nL and an effective volume of 200 nL which is twice compared to 100 nL of effective volume of the existing 5184-well plate by WaferGen. It is an important advantage that the 5184-well plate of the present disclosure has a larger volume which allows all the reactions of the present method can be carried out in a well of such a 5184-well plate, so that the procedure of the library construction is simplified and its efficiency is improved.

In addition, the 5184-well plate allows the reaction system of MDA in each well is in a volume less than 100 nL, so that the reaction system is greatly decreased compared to that presented in the existing 384-well plate, therefore the bias caused by MDA reaction is significantly reduced and the accuracy of the sequencing library is significantly improved.

It should be noted that, different biological samples can be reacted in the 5184-well plate at the same time by a variety of distribution patterns of the 5184-well plate, for example but not limited to in a pattern of 2×2592, 3×1728, 4×1296, 6×864, 8×648, 12×432, 16×324 and so on, without interfering with each other, thus the throughput of sequencing libraries is improved and the cost for library construction is shortened.

In addition, likelihood of separation patterns of the 5184-well plate can be further increased by virtual separation, for example first different tags such as 5184 different first and second tags such as 72 different first tags and 72 different second tags, are introduced in the process of PCR amplification, thus the combination in each well of the 5184-well plate is enormous depending on the kinds of tags.

In some embodiments of the present disclosure, the probability that the DNA fragment in each well of the 5184-well plate comes from same locus of parental chromosomes is lower than 1%. FIG. 5 is a schematic graph showing the probability of the homologous chromosomes in each well of the 5184-well plate as a function of the number of cells according to an exemplary embodiment of the present disclosure. As can be seen, as the number of cells increases, the probability increases, and the probability is lower than 1% when the number of cells is not more than 300. Thus, in order to ensure the probability of the homologous chromosomes in each well of the 5184-well plate lower than 1%, the genomic DNA fragment used as the starting material in embodiments of the present disclosure is in an amount from 100 to 1000 pg (equal to 15 to 200 of cells). In an embodiment of the present disclosure, 150 pg genomic DNA fragment is used to ensure the probability of the homologous chromosomes in each well of the 5184-well plate lower than 1%.

In the present disclosure, the 5184-well plate specific to the present method can significantly increase the number of wells, resulting in the amount of genomic DNA fragment in each well is much less compared to the current well plates such as 384-well plate and so on, so that the probability of the homologous chromosomes in each well of the 5184-well plate is decreased which is beneficial to decrease the heterozygosity of the amplified product, and the deviations arising during MDA is also reduced which can improve the accuracy of library, therefore the efficiency and the accuracy of genome assembly are greatly improved.

In another aspect of the present disclosure, provided is a method of constructing a sequencing library in a 5184-well plate, comprising 1) providing a single-stranded DNA fragment from a biological sample; 2) distributing the single-stranded DNA fragment to each well of the 5184-well plate, in which the single-stranded DNA fragment in each well comprises 1% genome of the biological sample; 3) subjecting the single-stranded DNA fragment in each well of the 5184-well plate to whole genomic amplification to obtain a whole genome amplification product, in which a reaction system in each well is in a volume less than 100 nL; 4) fragmenting the whole genome amplification product in each well of the 5184-well plate using a transposase embedded with two adaptors to obtain a fragmented product with two adaptors respectively at two ends; and 5) amplifying the fragmented product with two adaptors respectively at two ends in each well of the 5184-well plate using a tag sequence and a pair of primers to obtain said sequencing library, in which the tag sequence comprises a first tag sequence and a second tag sequence, and the first tag sequence is composed of a third adaptor, a first random fragment and a first single-stranded DNA sequence in order from the 5' end to the 3' end, and the second tag sequence is composed of a fourth adaptor, a second random fragment and a second single-stranded DNA sequence in order from the 5' end to the 3' end, in which the first tag sequence comprises 72 tag sequences containing different said first random fragments respectively, and the second tag sequence comprises 72 tag sequences containing different said second random fragments respectively.

In an embodiment, in the case that the biological sample is human genomic DNA, the step 1) of the method further comprises extracting a genomic DNA fragment from the biological sample, in which the genomic DNA fragment has a length not less than 100 kb; and subjecting the genomic DNA fragment to denaturation in an alkaline solution such as a potassium hydroxide solution at 20° C. to 30° C. such as 25° C. for 1 minute to 3 minutes such as 2 minutes to obtain the single-stranded DNA fragment. In another embodiment, in the case that the biological sample is microorganism, the step 1) of the method further comprises lysing the biological sample in an alkaline solution such as a potassium hydroxide solution at 80° C. to 90° C. such as 85° C. for 1 minute to 3 minutes such as 2 minutes to obtain a single-stranded DNA fragment. The microorganism mixture is distributed into the 5184-well plate before lysed in the alkaline solution. In specific, after diluted to be of an extreme low concentration by limiting dilution method, suspension of the microorganism mixture is distributed to wells of the 5184-well plate. For all 5184 wells, one third wells each includes only one single microorganism cell which can be used for constructing the whole genome library of the microorganism; another one third wells includes two or more cells; and the last one third wells includes no cell, such that the cell numbers in all cells conform Poisson distribution.

In some embodiments of present disclosure, 72 first tag sequences and 72 second tag sequences are applied to the each well of the 5184-well plate by distributing 72 first tag sequences to each well at columns of the 5184-well plate, allowing for the first tag sequence in each well at same columns is same but different at different columns, and distributing 72 second tag sequences to each well at rows of the 5184-well plate, allowing for the second tag sequence in each well at same rows is same but different at different rows, respectively. Therefore, 5184 sequencing libraries can be amplified using the present 5184-well plate and the present tag sequences, because a combination of the first tag sequence and the second tag sequence in each well of the 5184-well plate is different, so that the time consumed for the library construction is shorten and its efficiency is improved.

According to the present disclosure, high-throughput sequencing library of the single-cell can be constructed in embodiments of the present method using an amount of a microorganism mixture as starting materials, so that the whole genome library of a single microorganism cell can be successfully constructed, and theoretically about 1000 sequencing libraries are constructed independently in parallel at one time based on those single-cells respectively contained in one third wells of the present 5184-well plate, thus the present method contributes to analyzing the microbial community structure, function or diversity of the microorganism mixture; and identifying specific species from the microorganism mixture, especially for the microorganism such as some species of bacteria which cannot be isolated by medium culture from a complex microorganism mixture.

Thus, such the present method definitely greatly benefits for the Metagenome research. Moreover, the present method can also be used for the single-cell genome sequencing by constructing high-throughput sequencing library of the single-cell, thereby improving efficiency and shortening cost.

In further another aspect of the present disclosure, provides is a packaged product customized for constructing a sequencing library in a length of 200 bp to 1100 bp, in which the packaged product comprises a 384-well plate, a 5184-well plate and a Nanodispenser, and each well of the 5184-well plate has a volume of 350 nL and an effective volume of 200 nL. In further another aspect of the present disclosure, provides is a sequencing library according to the present method.

In further another aspect of the present disclosure, provides is use of the 5184-well plate for library construction.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art or in accordance with the product instructions. If the manufacturers of reagents or instruments are not specified, the reagents or instruments may be commercially available, for example, from Illumina Company.

EXAMPLE

Example 1

Construction of Sequencing Library of Human Genome

1. Extraction of Genomic DNA Fragment

After extracted from leukocyte in human blood by RecoverEase™ DNA extraction Kit (Agilent), genomic DNA fragments was detected by agarose gel electrophoresis under a condition of 6 V/cm and 50-90 seconds along a direction of switching field for 20 hours, with those in a length not less than 100 kb selected as a starting material, serving as the template of the whole genome amplification. The purity and concentration of the selected genomic DNA fragments were detected by Spectrophotometer NanoDrop-2000. The genomic DNA fragment with high quality has a value of OD 260/280 from 1.8 to 2.0, and the concentration of the genomic DNA fragments was adjusted to 664.56 pg/μL for the next step.

2. Denaturation of the Genomic DNA Fragment to Obtain Single-Stranded DNA Fragment 9.57 μL of the genomic DNA fragment obtained in step 1 was added into a 1.5 mL centrifuge tube, followed by addition of 172.3 μL alkaline solution which has been diluted 1/10 (seen in Table 5). After mixed to be even, the reaction solution was stilled at room temperature for 1 to 3 minutes, preferably 2 minutes, thus achieving denaturation with a single-stranded DNA fragment obtained, which was transferred onto ice. It is noted that such a process should be completed within 5 minutes, thereby only destroying a hydrogen bond between two strands of the DNA molecule and avoiding the genomic DNA from damage.

TABLE 5

Formulation of the alkaline solution
Alkaline Solution

| Reagents | Amount |
| --- | --- |
| potassium hydroxide | 8960 mg |
| 500 mM EDTA | 2000 µL |
| Total | adding water up to 100 mL |

3. MDA Reaction of the Single-Stranded DNA Fragment 3.1 13.40 µL of the single-stranded DNA fragment obtained in step 2 was added with 49.78 µL random primers each consisting of 8 bases (1 mM), followed by still standing at room temperature for 2 minutes without thoroughly mixing. The resulting mixture was then added with 496.78 µL nuclease-free water up to a total volume of 560 µL.

3.2 The solution, obtained in step 3.2, was distributed into 8 to 384 wells, preferably 24 wells, in a 384-well plate using a Finntip™ pipette. In specific, such 24 wells are show as blue color in FIG. 6 in, which are located at the first 12 wells in each of the first and second columns. The resulting solution was distributed into these 24 wells in a distribution pattern of 2×4, with each wells containing 22 µL (equivalent to 18.41 pg of genomic DNA) of the solution.

3.3 The solutions, distributed in 24 wells of the 384-well plate in step 3.2, were further equally distributed by MultiSample NanoDispenser (WaferGen) into wells of a customized 5184-well plate by means of program "LFR 35 nL Single Sample dispensing. seq", with one well containing 35 nL (equivalent to 0.0293 pg of genomic DNA) of the solution. It is noted that since one nucleus of the human leukocyte contains 6.5 pg of genomic DNA, the total number of cells contained in the customized 5184-well plate is 23 cells.

3.4 After sealed with parafilm, the customized 5184-well plate containing the single-stranded genomic DNA obtained in step 3.3 was centrifuged at 3220×g for 5 minutes (Eppendorf 5810), followed by still standing at room temperature till use for the purpose of allowing the solution contained to be at bottom of wells.

Figures 6, 7, 8:
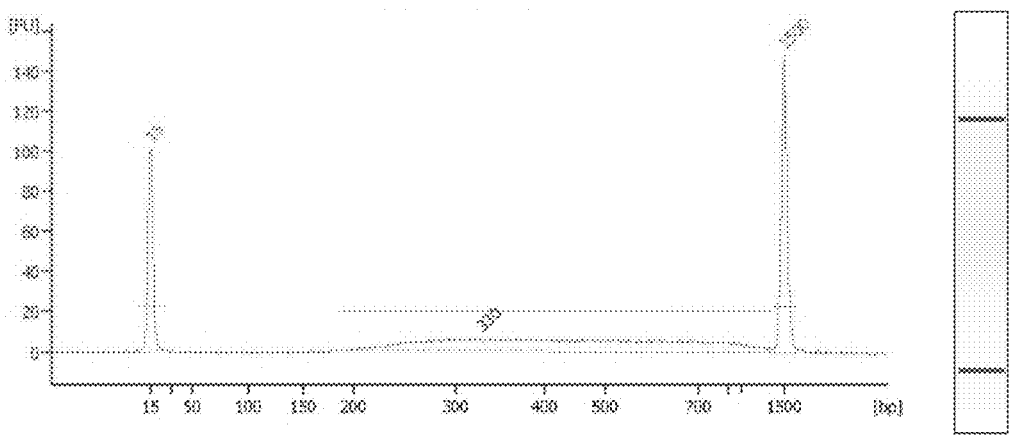
FIG. 6 is a schematic graph showing aliquots of the reaction solution added in a 384-well plate by a 4×2 multi-channel pipette according to some exemplary embodiments of the present disclosure.
FIG. 7 is a schematic graph showing aliquots of the tag sequences added in a 384-well plate by a 4×2 multi-channel pipette according to some exemplary embodiments of the present disclosure.
FIG. 8 is a schematic graph showing a distribution of a sequencing library detected by the Agilent Bioanalyzer according to the example 1 of the present disclosure.

3.5 A reaction buffer for MDA (i.e., whole genome amplification) was formulated to a 1.5 mL centrifuge tube in accordance with the components listed in Table 6, followed by shaken for mixing. After a brief centrifuge, the reaction buffer for MDA was distributed into those 24 wells in the 384-well plate as shown in FIG. 6, with one well containing 22 µL of the reaction buffer.

TABLE 6

Reaction buffer for MDA reaction

| Reagents | Volume (µL) |
| --- | --- |
| ddH₂O | 421.92 |
| 10 × Phi Buffer (Enzymatics #B7020) | 110.21 |
| 10% Pluronic F68 | 1.18 |
| 25 mM dNTP | 11.85 |
| Phi29 (Enzymatics #P7020-LC-L) | 14.81 |

3.6 After the parafilm was carefully removed, the customized 5184-well plate containing the single-stranded genomic DNA by step 3.3 was added, by MultiSample NanoDispenser (WaferGen), with the reaction buffers, which was equally distributed in 24 wells of the 384-well plate in step 3.5, by means of program "LFR 35 nL Single Sample dispensing. seq".

3.7 After sealed with parafilm again, the customized 5184-well plate containing the single-stranded genomic DNA and the reaction buffer obtained in step 3.6 was centrifuged at 3220×g for 5 minutes (Eppendorf 5810), followed by incubation in a warm bath at 30° C. for 60 minutes (or at 37° C. for 45 minutes); then at 65° C. for 5 minutes; and finally cooled down to room temperature for use, thereby obtaining the whole genome amplification product contained in wells of the 5184-well plate.

4. Fragmentation of the Whole Genome Amplification Product

The whole genome amplification product obtained in step 3.6 was fragmented to have a length of 200 bp to 1500 bp using a transposase embedded with a first adaptor and a second adaptor.

4.1 A reaction solution containing the transposase embedded with the first adaptor and the second adaptor (each having a sequence as shown in Table 1) was formulated in a 1.5 mL centrifuge tube, followed by shaken up and down for at least twenty times. After a brief centrifuge, the resulting reaction solution was distributed into 24 wells in the 384-well plate (as shown in FIG. 6), with one well containing 22 µL of the reaction solution.

TABLE 7

Reaction solution containing the transposase embedded
with the first adaptor and the second adaptor

| Reagents | Volume (µL) |
| --- | --- |
| 5 × Tagment Buffer (Vazyme # TD108-02) | 336.00 |
| Tagment Enzyme Mix* (Vazyme # TD108-02) | 224.00 |

4.2 After the parafilm was carefully removed, the customized 5184-well plate containing the whole genome amplification product obtained after step 3.6, was added, by MultiSample NanoDispenser (WaferGen), with the reaction solutions, which was equally distributed in 24 wells of the 384-well plate in step 4.1, by means of program "LFR 35 nL Single Sample dispensing. seq".

4.3 After sealed with parafilm again, the customized 5184-well plate containing the whole genome amplification product and the reaction solution obtained in step 4.2 was centrifuged at 3220×g for 5 minutes (Eppendorf 5810), followed by incubation in a warm bath at 55° C. for 10 minutes; and then cooled down to room temperature, thereby obtaining a fragmented product with two adaptors respectively at two ends for use.

4.4 A transesterase stop buffer was formulated in a 1.5 mL centrifuge tube in accordance with the components listed in Table 8, followed by shaken for mixing. After a brief centrifuge, the transesterase stop buffer was distributed into 24 wells in the 384-well plate (as shown in FIG. 6), with one well containing 14 µL of the transesterase stop buffer.

TABLE 8 transesterase stop buffer

| Reagents | Volume (µL) |
| --- | --- |
| 5 × NT buffer (Vazyme # TD108-02) | 823.2 |
| ddH₂O | 164.64 |

4.5 After the parafilm was carefully removed, the customized 5184-well plate containing the fragmented product with two adaptors respectively at two ends obtained in step 4.3 was added, by MultiSample NanoDispenser (Wafer- Gen), with the transesterase stop buffer, which was equally distributed in 24 wells of the 384-well plate in step 4.4, by means of program "LFR 35 nL Single Sample dispensing. seq", thereby obtaining fragmented product having a length of 200 bp to 1500 bp contained in the 5184-well plate.

The length of the fragmented product was detected by capillary electrophoresis (Agilent Bioanalyzer 2100). As can be seen from the result shown in FIGS. 9 and 10, the fragmented product have a length of 200 bp to 1500 bp.

5. Addition of Tag Sequences to the Fragmented Product with Two Adaptors Respectively at Two Ends 5.1 72 first tag sequences (2.5 μmol/L) contained in wells of a 96-well plate were distributed into 72 wells in a 384-well plate (shown as green color in FIG. 7) using an eight-channel pipette. After shaken for mixing, the 384-well plate containing the 72 first tag sequences was centrifuged at 3220×g for 5 minutes (Eppendorf 5810), followed by checked with no bubbles and preserved at room temperature for use. The 72 first tag sequences were equally distributed into 5184 wells of the customized 5184-well plate containing the fragmented product with two adaptors respectively at two ends obtained in step 4.5 using MultiSample NanoDispenser (WaferGen), allowing for the first tag sequence in each well at same columns is same but different at different columns. The first tag sequence has a sequence shown in Table 2.

5.2 In the same way, 72 second tag sequences (2.5 μmol/L) contained in wells of a 96-well plate were distributed into 72 wells in a 384-well plate (shown as green color in FIG. 7) using an eight-channel pipette. After shaken for mixing, the 384-well plate containing the 72 second tag sequences was centrifuged at 3220×g for 5 minutes (Eppendorf 5810), followed by checked with no bubbles and preserved at room temperature for use. The 72 second tag sequences were equally distributed into 5184 wells of the customized 5184-well plate containing the fragmented product with two adaptors respectively at two ends obtained in step 4.5 using MultiSample NanoDispenser (WaferGen), allowing for the second tag sequence in each well at same rows is same but different at different rows. The second tag sequence has a sequence shown in Table 3.

5.3 After sealed with parafilm again, the customized 5184-well plate containing the fragmented product and the tag sequences obtained in step 5.2 was centrifuged at 3220×g for 5 minutes (Eppendorf 5810), followed by incubation at room temperature for 10 min.

5.4 A PCR reaction solution was formulated in a 1.5 mL centrifuge tube in accordance to the components listed in Table 9, in which the first primer and the second primer each have a sequence as shown in Table 4, followed by shaken for mixing. After a brief centrifuge, the PCR reaction solution was distributed into 24 wells in the 384-well plate (shown as blue green color in FIG. 7), with one well containing 15.6 μL of the transesterase stop buffer.

5.5 The solutions, distributed in 24 wells of the 384-well plate in step 5.4, were further equally distributed by MultiSample NanoDispenser (WaferGen) into wells of the customized 5184-well plate after step 5.3 by means of program "LFR 35 nL Single Sample dispensing. seq".

TABLE 9

| PCR reaction solution | |
|---|---|
| Reagents | Volume (μL) |
| 5 × TruePrep Amplify Buffer | 865.83 |
| TruePrep Amplify Enzyme (1 U/μl) | 93.4185 |
| dNTP (10 mM) | 93.4185 |
| the first primer 100 μM | 15.9495 |

TABLE 9-continued

| PCR reaction solution | |
|---|---|
| Reagents | Volume (μL) |
| the second primer 100 μM | 15.9495 |
| ddH$_2$O | 22.785 |

5.6 The reaction mixture in each well of the 5184-well plate was centrifuged in eppendorf centrifuge 5810 at 3220×g for 5 minutes, and then subjected to PCR reaction according to the procedure shown in Table 10, thus obtaining the present sequencing library ligated with tag sequences.

TABLE 10

| Procedure of PCR reaction | | | |
|---|---|---|---|
| Steps | Temperature | | Time |
| 1 | 72° C. | | 3 min |
| 2 | 98° C. | 30 sec | 14 cycles |
|  | 98° C. | 10 sec |  |
|  | 60° C. | 30 sec |  |
|  | 72° C. | 3 min |  |
| 3 | 72° C. |  | 5 min |
| 4 | 4° C. |  | hold |

Note:
the temperature of lid is 105° C.

6. Sorting the Sequencing Library

Figure 9:
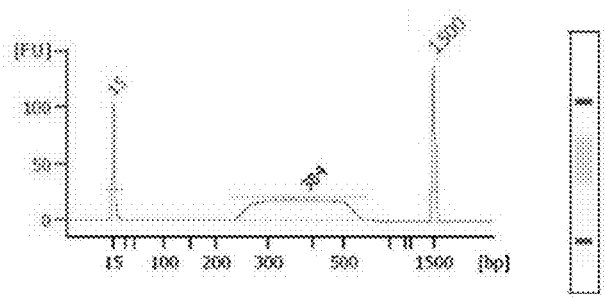
FIG. 9 is a schematic graph showing a distribution of the first library (250 bp to 550 bp) detected by the Agilent Bioanalyzer according to the example 1 of the present disclosure.
Figure 10:
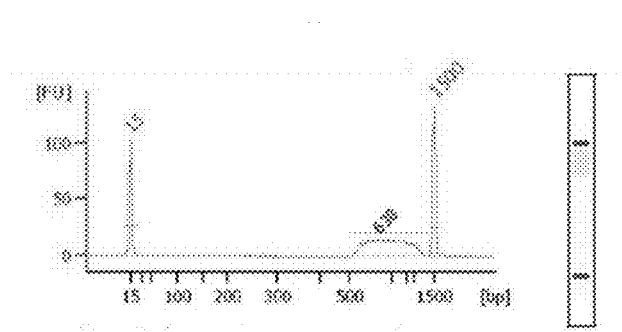
FIG. 10 is a schematic graph showing a distribution of the second library (550 bp to 1000 bp) detected by the Agilent Bioanalyzer according to the example 1 of the present disclosure.

The sequencing library was purified using 2% agarose gel electrophoresis, and then detected by the Agilent Bioanalyzer. The result is shown in FIG. 8. As can be seen, the sequencing library has a length between 200 bp to 1500 bp, and was concentrated in the regions of 250 to 550 bp and 550 bp to 1000 bp. The sequencing library in a length of 250 bp to 550 bp was sorted as a first library, and the sequencing library in a length of 550 bp to 1000 bp was sorted as a second library. The first library and the second library were detected by the Agilent Bioanalyzer, and the results are shown in FIGS. 9 and 10, respectively.

The concentration of the library was determined by qPCR according to the procedure shown in Table 11, and the result is shown in Table 12.

TABLE 11

| Procedure of qPCR | | | |
|---|---|---|---|
| steps | temperature | | time |
| 1 | 95° C. |  | 5 min |
| 2 | 95° C. | 30 sec | 35 cycles |
| 3 | 60° C. | 45 sec |  |

TABLE 12

| Concentrations of the first library and the second library | | | |
|---|---|---|---|
| NO. | standard concentration (nmol/L) | normalized concentration of qPCR (nmol/L) | conformity |
| the first library | >5 | 37.61 | Yes |
| the second library | >5 | 17.20 | Yes |

The results in Table 12 shows that the quality of the first library and the second library is satisfied and such libraries can be used for the next steps.

7. Sequencing and Assembly of the Sorted Library

Figure 11:
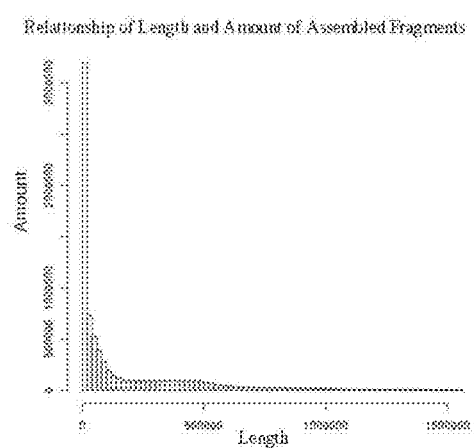
FIG. 11 is a schematic graph showing lengths of assembled fragments as a function of the number of assembled fragments according to the example 1 of the present disclosure.

The first library and the second library were sequenced using sequencer Hiseq 2000 or Hiseq 2500 (illumina), and the sequenced fragments were assembled by software SOAP2. The assembly results of the sequencing libraries of human genomic DNA fragment were shown in Table 12 and FIG. 11.

TABLE 12

Length of fragments formed by assembly of sequencing libraries

|  | median (bp) | average (bp) | standard deviation (bp) | maximum (bp) |
|---|---|---|---|---|
| length of fragments | 45,510 | 195,457 | 551,263 | 147,859,018 |

As can be seen from Table 12 and FIG. 12, the fragments formed by assembly of sequencing libraries have an average length of 195,457 bp, and a maximum length up to 147,859,018 bp. Thus, the sequencing library of a genomic DNA fragment in a length not less than 100 kb can be successfully constructed according to the present method.

Example 2

Construction of Sequencing Library of Genome in Microorganism

1. Isolation of Microorganism 1.1 Acquisition of a Microorganism Mixture 0.2 g fowl manure containing a mixture of microorganisms was added into a 1.5 mL centrifuge tube, followed by addition of 1000 μL phosphate buffer. The resulting solution was vortexed for 5 minutes and centrifuged at 10,000 rpm for 5 minutes, thus obtaining supernatant and precipitate. After discarding the supernatant, to the precipitate was added 8004, phosphate buffer, and the solution thus obtained was vortexed for 3 minutes and centrifuged at 2,000 rpm for 3 minutes for thoroughly mixing; with the obtained supernatant transferred into a new 1.5 mL centrifuge tube (such a step was repeated twice). The combined supernatants were centrifuged at 10,000 rpm for 5 minutes. After discarding obtained supernatant, to the remaining precipitate was added 800 μL phosphate buffer, with the resulting solution vortexed for 3 minutes for thoroughly mixing (such a step was repeated twice). The solution thus obtained was filtered by cellulose acetate filter membrane in a pore size of 20 μm. The filtrate was collected, transferred into a new centrifuge tube, and centrifuged at 10,000 rpm for 5 minutes. The resulting supernatant was discarded, thus obtaining a microorganism mixture.

1.2 Immobilization of Cells in the Microorganism Mixture

To the mixture of microorganisms was added 800 μL of 4% paraformaldehyde solution formulated by sterile water. The thus obtained solution was vortexed for 3 minutes for thoroughly mixing, and left at 4° C. overnight, thus obtaining immobilized cells of microorganisms.

1.3 Acquisition of Diluted Solution Containing Microorganism Cells

The immobilized cells of microorganisms were counted by hemocytometer, and diluted by sterile water to obtain a solution containing 30 microorganism cells per microliter.

2. Cell Lysis for Obtaining a Single-Stranded DNA Fragment 2.1 20 μL alkaline stock solution in Table 5 was diluted ⅓₀ with sterile water, with a total volume of 600 μL. The diluted alkaline solution was equally distributed into 24 wells of a 384-well plate as the manner shown as blue in FIG. 6 with one well containing 22 μL, and then equally distributed by MultiSample NanoDispenser (WaferGen) into each well of a customized 5184-well plate, with each well having a volume of 350 nL.

2.2 After sealed with parafilm, the customized 5184-well plate containing the diluted alkaline solution obtained in step 2.1 was centrifuged at 4000×g for 5 minutes (Eppendorf 5810), followed by incubation in a metal bath at 85° C. for 10 min after carefully removing the parafilm, so as to remove the water and then cooled down to room temperature.

2.3 After diluted to be of an extreme low concentration by limiting dilution method, suspension of the microorganism mixture is distributed to equally distributed into those 24 wells of the 384-well plate as the manner shown as blue in FIG. 6 with one well containing 22 μL, and then equally distributed by MultiSample NanoDispenser (WaferGen) into each well of the customized 5184-well plate obtained after step 2.2 by means of program "LFR 35 nL Single Sample dispensing. seq", with each well having a volume of 350 nL.

2.4 After sealed with parafilm again, the customized 5184-well plate obtained in step 2.3 was centrifuged at 4000×g for 5 minutes (Eppendorf 5810), followed by incubation in a suitable warm bath at 85° C. for 2 minutes. Such centrifuge and incubation were repeated once more, thus obtaining a single-stranded DNA fragment.

3. MDA Reaction of the Single-Stranded DNA Fragment

All steps for MDA are same as that in Example 1, except for incubation at 37° C. for 10 hours.

4. Fragmentation of the Whole Genome Amplification Product

All steps for fragmentation are same as that in Example 1.

5. Addition of Tag Sequences to the Fragmented Product with Two Adaptors Respectively at Two Ends All steps for addition of tag sequences are same as that in Example 1.

6. Sorting the Sequencing Library Ligated with Two Tag Sequences

All steps for sorting are same as that in Example 1.

7. Sequencing and Assembly of the Sorted Library

All steps for sequencing are same as that in Example 1.

The results show that the whole genome of a species of bacteria was successfully assembled.

INDUSTRIAL APPLICABILITY

According to embodiments of the present disclosure, the sequencing library of a long fragment in a length not less than 100 kb is constructed using a genomic DNA fragment from the biology sample in an amount of 150 pg, in combination of multiple displacement amplification (MDA) and fragmentation by transposase, and based on nano-scale pipetting platform, thereby both optimizing the procedure of library construction and improving the accuracy of library assembly.

According to embodiments of the present disclosure, high-throughput sequencing library of the single-cell can be constructed by the present method using the amount of the microorganism mixture as starting materials, so that the whole genome library of the single microorganism cell can be successfully constructed, and theoretically about 1000 sequencing libraries are constructed independently in parallel at one time based on those single-cells respectively contained in one third wells of the present 5184-well plate, thus the present method contributes to analyzing the microbial community structure, function or diversity of the microorganism mixture, and identifying specific species from the microorganism mixture, especially for the microorganism such as some species of bacteria which cannot be isolated by medium culture from a complex microorganism mixture. Thus, such the present method definitely greatly benefits for the Metagenome research. According to embodiments of the present disclosure, the Illumina's sequencing library is constructed by genome fragmentation, end-repairing the fragmented DNA fragment, adenine addition to the terminal, adaptor ligation, PCR amplification and product purification, and a total of 1.5 days is consumed for the library construction, in which a manual process takes 5 hours; the Fosmid haplotype library is constructed by host cell infection by expression vector, isolation and culture of the transformed host cell, extraction of genome in positive clone, sequencing library construction and library sorting, and a total of 8 days is consumed for the library construction, in which a manual process takes 4.5 days; the SLRH (statistically aided, long-read haplotyping) haplotype library is constructed by genome fragmentation, selection and isolation of fragmented DNA fragment and qPCR detection, and then Long PCR reaction, fragmentation by transposase and PCR amplification, finally amplified library collection and sorting, and a total of 3 days is consumed for the library construction, in which a manual process takes 1 day; while in embodiments of the present disclosure, a sequencing library is constructed by genome amplification, fragmentation by transposase, PCR amplification and amplified library collection and sorting, and a total of 1.5 days is consumed for the library construction, in which a manual process takes 3.5 hours. Thus, compared to the methods of library construction in the related art, the steps of library construction according to the present method is reduced, therefore shortening the total time consumed for the library construction and improving efficiency of the library construction.

Reference throughout this specification to "an embodiment", "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example" or "in some examples" in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A customized 5184-well plate-based method of constructing a sequencing library in a length ranging from 550 bp to 1000 bp, comprising steps of:
   1) providing a single-stranded DNA fragment from a biological sample and distributing the single-stranded DNA fragments extracted from 10 to 500 cells into said 5184-well plate such that a probability of homologous chromosome fragments deriving from both mother and father at the same site in their respective genomes presenting in each well is less than 1%;
   2) subjecting the single-stranded DNA fragment to whole genomic amplification to obtain a whole genome amplification product;
   3) fragmenting the whole genome amplification product using a transposase embedded with two adaptors to obtain a fragmented product with two adaptors respectively at two ends; and
   4) amplifying the fragmented product with two adaptors respectively at two ends using a tag sequence and a pair of primers to obtain said sequencing library,
   wherein each well of said 5184-well plate has a volume of 350 nL and an effective volume of 200 nL.

2. The method according to claim 1, wherein the biological sample is derived from a plant, an animal or a microorganism.

3. The method according to claim 1, wherein the step of providing the single-stranded DNA fragment from the biological sample further comprises:
   extracting a genomic DNA fragment from the biological sample, wherein the genomic DNA fragment has a length not less than 100 kb; and
   subjecting the genomic DNA fragment to denaturation in an alkaline solution at 20° C. to 30° C. for 1 minute to 3 minutes to obtain the single-stranded DNA fragment.

4. The method according to claim 3, wherein the genomic DNA fragment is in an amount of 100 pg to 1000 pg.

5. The method according to claim 1, wherein the step of extracting the single-stranded DNA fragment from the biological sample further comprises:
   incubating the biological sample in an alkaline solution at 80° C. to 90° C. for 1 to 3 minutes to obtain the single-stranded DNA fragment.

6. The method according to claim 1, wherein the whole genome amplification is multiple displacement amplification (MDA).

7. The method according to claim 6, wherein the multiple displacement amplification is carried out by incubation of the single-stranded DNA fragment first at 30° C. to 37° C. for 45 minute to 60 minutes and then at 65° C. for 5 minutes in the presence of random primers.

8. The method according to claim 7, wherein the random primers each have a length of 5 bp to 20 bp.

9. The method according to claim 1, wherein the transposase is embedded with a first adaptor and a second adaptor, and the first adaptor is of a sequence different from that of the second sequence.

10. The method according to claim 9, wherein the first adaptor comprises a first long-chain sequence and a first short-chain sequence, and the first long-chain sequence is composed of a region unpaired with the first short-chain sequence and a region paired with the first short-chain sequence in order from the 5' end to the 3' end; and
  the second adaptor comprises a second long-chain sequence and a second short-chain sequence, and the second long-chain sequence is composed of a region unpaired with the second short-chain sequence and a region paired with the second short-chain sequence in order from the 5' end to the 3' end.

11. The method according to claim 1, wherein the whole genome amplification product is fragmented by incubation of the whole genome amplification product at 50° C. to 60° C. for 5 minute to 20 minutes in the presence of the transposase embedded with two adaptors.

12. The method according to claim 1, wherein the fragmented product with two adaptors respectively at two ends has a length in a range of 300 bp to 1000 bp.

13. The method according to claim 10, wherein the tag sequence comprises a first tag sequence and a second tag sequence,
  wherein the first tag sequence is composed of a third adaptor, a first random fragment and a first single-stranded DNA sequence in order from the 5' end to the 3' end; and the second tag sequence is composed of a fourth adaptor, a second random fragment and a second single-stranded DNA sequence in order from the 5' end to the 3' end,
  wherein the first single-stranded DNA sequence is identical to the region unpaired with the first short-chain sequence of the first long-chain sequence of the first adaptor; and the second single-stranded DNA sequence is identical to the region unpaired with the second short-chain sequence of the second long-chain sequence of the second adaptor.

14. The method according to claim 13, wherein the first random fragment and the second random fragment each have a length of 5 bp to 20 bp.

15. The method according to claim 13, wherein the pair of primers comprise a first primer and a second primer, wherein the first primer is of a sequence is identical or complementary to part of the sequence of the third adaptor; and the second primer is of a sequence identical or complementary to part of the sequence of the fourth adaptor.

16. The method according to claim 1, further comprising:
  sorting the sequencing library by magnetic beads or agarose electrophoresis to obtain the desired sequencing library in the length ranging from 550 bp to 1000 bp.

17. A method of constructing a sequencing library in a length ranging from 550 bp to 1000 bp using a customized 5184-well plate, comprising:
  1) providing a single-stranded DNA fragment from a biological sample;
  2) distributing the single-stranded DNA fragments extracted from 10 to 500 cells into said 5184-well plate such that a probability of homologous chromosome fragments deriving from both mother and father at the same site in their respective genomes presenting in each well is less than 1%;
  3) subjecting the single-stranded DNA fragment in each well of said 5184-well plate to whole genomic amplification to obtain a whole genome amplification product, wherein a reaction system in each well is in a volume less than 100 nL;
  4) fragmenting the whole genome amplification product in each well of said 5184-well plate using a transposase embedded with two adaptors to obtain a fragmented product with two adaptors respectively at two ends; and
  5) amplifying the fragmented product with two adaptors respectively at two ends in each well of said 5184-well plate using a tag sequence and a pair of primers to obtain said sequencing library,
  wherein the tag sequence comprises a first tag sequence and a second tag sequence,
  wherein the first tag sequence is composed of a third adaptor, a first random fragment and a first single-stranded DNA sequence in order from the 5' end to the 3' end; and the second tag sequence is composed of a fourth adaptor, a second random fragment and a second single-stranded DNA sequence in order from the 5' end to the 3' end,
  wherein the first tag sequence comprises 72 tag sequences containing different said first random fragments respectively, and
  the second tag sequence comprises 72 tag sequences containing different said second random fragments respectively,
  wherein each well of said 5184-well plate has a volume of 350 nL and an effective volume of 200 nL.

18. The method according to claim 1, wherein the probability of homologous chromosome fragments derived from both mother and father at the same site in their respective genomes presenting in one same well satisfies the formula below:

$$P = \sum_{x=2}^{\infty} p(x), \; p(x) = \frac{e^{-\lambda} \cdot \lambda^x}{x!},$$

wherein "x" represent a sequencing depth of a single base site; and $\lambda = 4n/w$, where $\lambda$ represents the amount of genome, n represents the cell number, and w represents the number of wells.

* * * * *

SEQUENCE LISTING

```
<160> NUMBER OF SEQ ID NOS: 152

<210> SEQ ID NO 1
<211> LENGTH: 47
<212> TYPE: DNA
<213> ORGANISM: Artificial Sequence
<220> FEATURE:
<223> OTHER INFORMATION: first tag sequence: N701

<400> SEQUENCE: 1
caagcagaag acggcatacg agattcgcct tagtctcgtg ggctcgg                47

<210> SEQ ID NO 2
<211> LENGTH: 47
<212> TYPE: DNA
<213> ORGANISM: Artificial Sequence
<220> FEATURE:
<223> OTHER INFORMATION: first tag sequence: N702

<400> SEQUENCE: 2
caagcagaag acggcatacg agatctagta cggtctcgtg ggctcgg                47

<210> SEQ ID NO 3
<211> LENGTH: 47
<212> TYPE: DNA
<213> ORGANISM: Artificial Sequence
<220> FEATURE:
<223> OTHER INFORMATION: first tag sequence: N703

<400> SEQUENCE: 3
caagcagaag acggcatacg agatttctgc ctgtctcgtg ggctcgg                47
```

```
<210> SEQ ID NO 4
<211> LENGTH: 47
<212> TYPE: DNA
<213> ORGANISM: Artificial Sequence
<220> FEATURE:
<223> OTHER INFORMATION: first tag sequence: N704

<400> SEQUENCE: 4
caagcagaag acggcatacg agatgctcag gagtctcgtg ggctcgg                   47

<210> SEQ ID NO 5
<211> LENGTH: 47
<212> TYPE: DNA
<213> ORGANISM: Artificial Sequence
<220> FEATURE:
<223> OTHER INFORMATION: first tag sequence: N705

<400> SEQUENCE: 5
caagcagaag acggcatacg agataggagt ccgtctcgtg ggctcgg                   47

<210> SEQ ID NO 6
<211> LENGTH: 47
<212> TYPE: DNA
<213> ORGANISM: Artificial Sequence
<220> FEATURE:
<223> OTHER INFORMATION: first tag sequence: N706

<400> SEQUENCE: 6
caagcagaag acggcatacg agatcatgcc tagtctcgtg ggctcgg                   47

<210> SEQ ID NO 7
<211> LENGTH: 47
<212> TYPE: DNA
<213> ORGANISM: Artificial Sequence
<220> FEATURE:
<223> OTHER INFORMATION: first tag sequence: N707

<400> SEQUENCE: 7
caagcagaag acggcatacg agatgtagag aggtctcgtg ggctcgg                   47

<210> SEQ ID NO 8
<211> LENGTH: 47
<212> TYPE: DNA
<213> ORGANISM: Artificial Sequence
<220> FEATURE:
<223> OTHER INFORMATION: first tag sequence: N708

<400> SEQUENCE: 8
caagcagaag acggcatacg agatcctctc tggtctcgtg ggctcgg                   47

<210> SEQ ID NO 9
<211> LENGTH: 47
<212> TYPE: DNA
<213> ORGANISM: Artificial Sequence
<220> FEATURE:
<223> OTHER INFORMATION: first tag sequence: N709

<400> SEQUENCE: 9
caagcagaag acggcatacg agatagcgta gcgtctcgtg ggctcgg                   47

<210> SEQ ID NO 10
<211> LENGTH: 47
<212> TYPE: DNA
<213> ORGANISM: Artificial Sequence
<220> FEATURE:
<223> OTHER INFORMATION: first tag sequence: N710
```

<400> SEQUENCE: 10
caagcagaag acggcatacg agatcagcct cggtctcgtg ggctcgg        47

<210> SEQ ID NO 11
<211> LENGTH: 47
<212> TYPE: DNA
<213> ORGANISM: Artificial Sequence
<220> FEATURE:
<223> OTHER INFORMATION: first tag sequence: N711

<400> SEQUENCE: 11
caagcagaag acggcatacg agattgcctc ttgtctcgtg ggctcgg        47

<210> SEQ ID NO 12
<211> LENGTH: 47
<212> TYPE: DNA
<213> ORGANISM: Artificial Sequence
<220> FEATURE:
<223> OTHER INFORMATION: first tag sequence: N712

<400> SEQUENCE: 12
caagcagaag acggcatacg agattcctct acgtctcgtg ggctcgg        47

<210> SEQ ID NO 13
<211> LENGTH: 47
<212> TYPE: DNA
<213> ORGANISM: Artificial Sequence
<220> FEATURE:
<223> OTHER INFORMATION: first tag sequence: N713

<400> SEQUENCE: 13
caagcagaag acggcatacg agataagcaa tggtctcgtg ggctcgg        47

<210> SEQ ID NO 14
<211> LENGTH: 47
<212> TYPE: DNA
<213> ORGANISM: Artificial Sequence
<220> FEATURE:
<223> OTHER INFORMATION: first tag sequence: N714

<400> SEQUENCE: 14
caagcagaag acggcatacg agataatccg aagtctcgtg ggctcgg        47

<210> SEQ ID NO 15
<211> LENGTH: 47
<212> TYPE: DNA
<213> ORGANISM: Artificial Sequence
<220> FEATURE:
<223> OTHER INFORMATION: first tag sequence: N715

<400> SEQUENCE: 15
caagcagaag acggcatacg agataatgat gagtctcgtg ggctcgg        47

<210> SEQ ID NO 16
<211> LENGTH: 47
<212> TYPE: DNA
<213> ORGANISM: Artificial Sequence
<220> FEATURE:
<223> OTHER INFORMATION: first tag sequence: N716

<400> SEQUENCE: 16
caagcagaag acggcatacg agatacagga gcgtctcgtg ggctcgg        47

<210> SEQ ID NO 17
<211> LENGTH: 47

```
<212> TYPE: DNA
<213> ORGANISM: Artificial Sequence
<220> FEATURE:
<223> OTHER INFORMATION: first tag sequence: N717

<400> SEQUENCE: 17
caagcagaag acggcatacg agataccgag ctgtctcgtg ggctcgg            47

<210> SEQ ID NO 18
<211> LENGTH: 47
<212> TYPE: DNA
<213> ORGANISM: Artificial Sequence
<220> FEATURE:
<223> OTHER INFORMATION: first tag sequence: N718

<400> SEQUENCE: 18
caagcagaag acggcatacg agatacctgt tggtctcgtg ggctcgg            47

<210> SEQ ID NO 19
<211> LENGTH: 47
<212> TYPE: DNA
<213> ORGANISM: Artificial Sequence
<220> FEATURE:
<223> OTHER INFORMATION: first tag sequence: N719

<400> SEQUENCE: 19
caagcagaag acggcatacg agataccttg aagtctcgtg ggctcgg            47

<210> SEQ ID NO 20
<211> LENGTH: 47
<212> TYPE: DNA
<213> ORGANISM: Artificial Sequence
<220> FEATURE:
<223> OTHER INFORMATION: first tag sequence: N720

<400> SEQUENCE: 20
caagcagaag acggcatacg agatactacg tggtctcgtg ggctcgg            47

<210> SEQ ID NO 21
<211> LENGTH: 47
<212> TYPE: DNA
<213> ORGANISM: Artificial Sequence
<220> FEATURE:
<223> OTHER INFORMATION: first tag sequence: N721

<400> SEQUENCE: 21
caagcagaag acggcatacg agatactctt acgtctcgtg ggctcgg            47

<210> SEQ ID NO 22
<211> LENGTH: 47
<212> TYPE: DNA
<213> ORGANISM: Artificial Sequence
<220> FEATURE:
<223> OTHER INFORMATION: first tag sequence: N722

<400> SEQUENCE: 22
caagcagaag acggcatacg agatagaagg tagtctcgtg ggctcgg            47

<210> SEQ ID NO 23
<211> LENGTH: 47
<212> TYPE: DNA
<213> ORGANISM: Artificial Sequence
<220> FEATURE:
<223> OTHER INFORMATION: first tag sequence: N723

<400> SEQUENCE: 23
```
caagcagaag acggcatacg agatagagac ttgtctcgtg ggctcgg           47

<210> SEQ ID NO 24
<211> LENGTH: 47
<212> TYPE: DNA
<213> ORGANISM: Artificial Sequence
<220> FEATURE:
<223> OTHER INFORMATION: first tag sequence: N724

<400> SEQUENCE: 24
caagcagaag acggcatacg agatagatct ctgtctcgtg ggctcgg           47

<210> SEQ ID NO 25
<211> LENGTH: 47
<212> TYPE: DNA
<213> ORGANISM: Artificial Sequence
<220> FEATURE:
<223> OTHER INFORMATION: first tag sequence: N725

<400> SEQUENCE: 25
caagcagaag acggcatacg agataggttc atgtctcgtg ggctcgg           47

<210> SEQ ID NO 26
<211> LENGTH: 47
<212> TYPE: DNA
<213> ORGANISM: Artificial Sequence
<220> FEATURE:
<223> OTHER INFORMATION: first tag sequence: N726

<400> SEQUENCE: 26
caagcagaag acggcatacg agatagtctg gtgtctcgtg ggctcgg           47

<210> SEQ ID NO 27
<211> LENGTH: 47
<212> TYPE: DNA
<213> ORGANISM: Artificial Sequence
<220> FEATURE:
<223> OTHER INFORMATION: first tag sequence: N727

<400> SEQUENCE: 27
caagcagaag acggcatacg agatagttat aggtctcgtg ggctcgg           47

<210> SEQ ID NO 28
<211> LENGTH: 47
<212> TYPE: DNA
<213> ORGANISM: Artificial Sequence
<220> FEATURE:
<223> OTHER INFORMATION: first tag sequence: N728

<400> SEQUENCE: 28
caagcagaag acggcatacg agatagttcc gcgtctcgtg ggctcgg           47

<210> SEQ ID NO 29
<211> LENGTH: 47
<212> TYPE: DNA
<213> ORGANISM: Artificial Sequence
<220> FEATURE:
<223> OTHER INFORMATION: first tag sequence: N729

<400> SEQUENCE: 29
caagcagaag acggcatacg agatataact aggtctcgtg ggctcgg           47

<210> SEQ ID NO 30
<211> LENGTH: 47
<212> TYPE: DNA
<213> ORGANISM: Artificial Sequence

```
<220> FEATURE:
<223> OTHER INFORMATION: first tag sequence: N730

<400> SEQUENCE: 30
caagcagaag acggcatacg agatatataa gagtctcgtg ggctcgg        47

<210> SEQ ID NO 31
<211> LENGTH: 47
<212> TYPE: DNA
<213> ORGANISM: Artificial Sequence
<220> FEATURE:
<223> OTHER INFORMATION: first tag sequence: N731

<400> SEQUENCE: 31
caagcagaag acggcatacg agatatcgat tcgtctcgtg ggctcgg        47

<210> SEQ ID NO 32
<211> LENGTH: 47
<212> TYPE: DNA
<213> ORGANISM: Artificial Sequence
<220> FEATURE:
<223> OTHER INFORMATION: first tag sequence: N732

<400> SEQUENCE: 32
caagcagaag acggcatacg agatatctta ttgtctcgtg ggctcgg        47

<210> SEQ ID NO 33
<211> LENGTH: 47
<212> TYPE: DNA
<213> ORGANISM: Artificial Sequence
<220> FEATURE:
<223> OTHER INFORMATION: first tag sequence: N733

<400> SEQUENCE: 33
caagcagaag acggcatacg agatatggca tagtctcgtg ggctcgg        47

<210> SEQ ID NO 34
<211> LENGTH: 47
<212> TYPE: DNA
<213> ORGANISM: Artificial Sequence
<220> FEATURE:
<223> OTHER INFORMATION: first tag sequence: N734

<400> SEQUENCE: 34
caagcagaag acggcatacg agatattaga atgtctcgtg ggctcgg        47

<210> SEQ ID NO 35
<211> LENGTH: 47
<212> TYPE: DNA
<213> ORGANISM: Artificial Sequence
<220> FEATURE:
<223> OTHER INFORMATION: first tag sequence: N735

<400> SEQUENCE: 35
caagcagaag acggcatacg agatcaacat tagtctcgtg ggctcgg        47

<210> SEQ ID NO 36
<211> LENGTH: 47
<212> TYPE: DNA
<213> ORGANISM: Artificial Sequence
<220> FEATURE:
<223> OTHER INFORMATION: first tag sequence: N736

<400> SEQUENCE: 36
caagcagaag acggcatacg agatcaagta acgtctcgtg ggctcgg        47
```

<210> SEQ ID NO 37
<211> LENGTH: 47
<212> TYPE: DNA
<213> ORGANISM: Artificial Sequence
<220> FEATURE:
<223> OTHER INFORMATION: first tag sequence: N737

<400> SEQUENCE: 37
caagcagaag acggcatacg agatcagtga atgtctcgtg ggctcgg        47

<210> SEQ ID NO 38
<211> LENGTH: 47
<212> TYPE: DNA
<213> ORGANISM: Artificial Sequence
<220> FEATURE:
<223> OTHER INFORMATION: first tag sequence: N738

<400> SEQUENCE: 38
caagcagaag acggcatacg agatcatatg atgtctcgtg ggctcgg        47

<210> SEQ ID NO 39
<211> LENGTH: 47
<212> TYPE: DNA
<213> ORGANISM: Artificial Sequence
<220> FEATURE:
<223> OTHER INFORMATION: first tag sequence: N739

<400> SEQUENCE: 39
caagcagaag acggcatacg agatcattaa gcgtctcgtg ggctcgg        47

<210> SEQ ID NO 40
<211> LENGTH: 47
<212> TYPE: DNA
<213> ORGANISM: Artificial Sequence
<220> FEATURE:
<223> OTHER INFORMATION: first tag sequence: N740

<400> SEQUENCE: 40
caagcagaag acggcatacg agatccatat ccgtctcgtg ggctcgg        47

<210> SEQ ID NO 41
<211> LENGTH: 47
<212> TYPE: DNA
<213> ORGANISM: Artificial Sequence
<220> FEATURE:
<223> OTHER INFORMATION: first tag sequence: N741

<400> SEQUENCE: 41
caagcagaag acggcatacg agatccatca aggtctcgtg ggctcgg        47

<210> SEQ ID NO 42
<211> LENGTH: 47
<212> TYPE: DNA
<213> ORGANISM: Artificial Sequence
<220> FEATURE:
<223> OTHER INFORMATION: first tag sequence: N742

<400> SEQUENCE: 42
caagcagaag acggcatacg agatccgatc ttgtctcgtg ggctcgg        47

<210> SEQ ID NO 43
<211> LENGTH: 47
<212> TYPE: DNA
<213> ORGANISM: Artificial Sequence
<220> FEATURE:
<223> OTHER INFORMATION: first tag sequence: N743

-continued

<400> SEQUENCE: 43
caagcagaag acggcatacg agatccggtt aagtctcgtg ggctcgg                47

<210> SEQ ID NO 44
<211> LENGTH: 47
<212> TYPE: DNA
<213> ORGANISM: Artificial Sequence
<220> FEATURE:
<223> OTHER INFORMATION: first tag sequence: N744

<400> SEQUENCE: 44
caagcagaag acggcatacg agatcgactt aggtctcgtg ggctcgg                47

<210> SEQ ID NO 45
<211> LENGTH: 47
<212> TYPE: DNA
<213> ORGANISM: Artificial Sequence
<220> FEATURE:
<223> OTHER INFORMATION: first tag sequence: N745

<400> SEQUENCE: 45
caagcagaag acggcatacg agatcgcgaa tagtctcgtg ggctcgg                47

<210> SEQ ID NO 46
<211> LENGTH: 47
<212> TYPE: DNA
<213> ORGANISM: Artificial Sequence
<220> FEATURE:
<223> OTHER INFORMATION: first tag sequence: N746

<400> SEQUENCE: 46
caagcagaag acggcatacg agatcgtgct tcgtctcgtg ggctcgg                47

<210> SEQ ID NO 47
<211> LENGTH: 47
<212> TYPE: DNA
<213> ORGANISM: Artificial Sequence
<220> FEATURE:
<223> OTHER INFORMATION: first tag sequence: N747

<400> SEQUENCE: 47
caagcagaag acggcatacg agatctactg gagtctcgtg ggctcgg                47

<210> SEQ ID NO 48
<211> LENGTH: 47
<212> TYPE: DNA
<213> ORGANISM: Artificial Sequence
<220> FEATURE:
<223> OTHER INFORMATION: first tag sequence: N748

<400> SEQUENCE: 48
caagcagaag acggcatacg agatctagac aagtctcgtg ggctcgg                47

<210> SEQ ID NO 49
<211> LENGTH: 47
<212> TYPE: DNA
<213> ORGANISM: Artificial Sequence
<220> FEATURE:
<223> OTHER INFORMATION: first tag sequence: N749

<400> SEQUENCE: 49
caagcagaag acggcatacg agattgtcga acgtctcgtg ggctcgg                47

<210> SEQ ID NO 50

```
<211> LENGTH: 47
<212> TYPE: DNA
<213> ORGANISM: Artificial Sequence
<220> FEATURE:
<223> OTHER INFORMATION: first tag sequence: N750

<400> SEQUENCE: 50
caagcagaag acggcatacg agatcgatag atgtctcgtg ggctcgg                47

<210> SEQ ID NO 51
<211> LENGTH: 47
<212> TYPE: DNA
<213> ORGANISM: Artificial Sequence
<220> FEATURE:
<223> OTHER INFORMATION: first tag sequence: N751

<400> SEQUENCE: 51
caagcagaag acggcatacg agataacagt aagtctcgtg ggctcgg                47

<210> SEQ ID NO 52
<211> LENGTH: 47
<212> TYPE: DNA
<213> ORGANISM: Artificial Sequence
<220> FEATURE:
<223> OTHER INFORMATION: first tag sequence: N752

<400> SEQUENCE: 52
caagcagaag acggcatacg agatccgcgt gtgtctcgtg ggctcgg                47

<210> SEQ ID NO 53
<211> LENGTH: 47
<212> TYPE: DNA
<213> ORGANISM: Artificial Sequence
<220> FEATURE:
<223> OTHER INFORMATION: first tag sequence: N753

<400> SEQUENCE: 53
caagcagaag acggcatacg agattctgga tagtctcgtg ggctcgg                47

<210> SEQ ID NO 54
<211> LENGTH: 47
<212> TYPE: DNA
<213> ORGANISM: Artificial Sequence
<220> FEATURE:
<223> OTHER INFORMATION: first tag sequence: N754

<400> SEQUENCE: 54
caagcagaag acggcatacg agattattcc tagtctcgtg ggctcgg                47

<210> SEQ ID NO 55
<211> LENGTH: 47
<212> TYPE: DNA
<213> ORGANISM: Artificial Sequence
<220> FEATURE:
<223> OTHER INFORMATION: first tag sequence: N755

<400> SEQUENCE: 55
caagcagaag acggcatacg agattcacgt tcgtctcgtg ggctcgg                47

<210> SEQ ID NO 56
<211> LENGTH: 47
<212> TYPE: DNA
<213> ORGANISM: Artificial Sequence
<220> FEATURE:
<223> OTHER INFORMATION: first tag sequence: N756

<400> SEQUENCE: 56
```
caagcagaag acggcatacg agataacgca atgtctcgtg ggctcgg    47

<210> SEQ ID NO 57
<211> LENGTH: 47
<212> TYPE: DNA
<213> ORGANISM: Artificial Sequence
<220> FEATURE:
<223> OTHER INFORMATION: first tag sequence: N757

<400> SEQUENCE: 57
caagcagaag acggcatacg agatgcttac gagtctcgtg ggctcgg    47

<210> SEQ ID NO 58
<211> LENGTH: 47
<212> TYPE: DNA
<213> ORGANISM: Artificial Sequence
<220> FEATURE:
<223> OTHER INFORMATION: first tag sequence: N758

<400> SEQUENCE: 58
caagcagaag acggcatacg agattacttc gcgtctcgtg ggctcgg    47

<210> SEQ ID NO 59
<211> LENGTH: 47
<212> TYPE: DNA
<213> ORGANISM: Artificial Sequence
<220> FEATURE:
<223> OTHER INFORMATION: first tag sequence: N759

<400> SEQUENCE: 59
caagcagaag acggcatacg agatcgcagt ccgtctcgtg ggctcgg    47

<210> SEQ ID NO 60
<211> LENGTH: 47
<212> TYPE: DNA
<213> ORGANISM: Artificial Sequence
<220> FEATURE:
<223> OTHER INFORMATION: first tag sequence: N760

<400> SEQUENCE: 60
caagcagaag acggcatacg agatcaatgc tcgtctcgtg ggctcgg    47

<210> SEQ ID NO 61
<211> LENGTH: 47
<212> TYPE: DNA
<213> ORGANISM: Artificial Sequence
<220> FEATURE:
<223> OTHER INFORMATION: first tag sequence: N761

<400> SEQUENCE: 61
caagcagaag acggcatacg agatcacggc gagtctcgtg ggctcgg    47

<210> SEQ ID NO 62
<211> LENGTH: 47
<212> TYPE: DNA
<213> ORGANISM: Artificial Sequence
<220> FEATURE:
<223> OTHER INFORMATION: first tag sequence: N762

<400> SEQUENCE: 62
caagcagaag acggcatacg agatcgccgc tggtctcgtg ggctcgg    47

<210> SEQ ID NO 63
<211> LENGTH: 47
<212> TYPE: DNA

<210> SEQ ID NO 63
<211> LENGTH: 47
<212> TYPE: DNA
<213> ORGANISM: Artificial Sequence
<220> FEATURE:
<223> OTHER INFORMATION: first tag sequence: N763

<400> SEQUENCE: 63
caagcagaag acggcatacg agatgcatcc ttgtctcgtg ggctcgg    47

<210> SEQ ID NO 64
<211> LENGTH: 47
<212> TYPE: DNA
<213> ORGANISM: Artificial Sequence
<220> FEATURE:
<223> OTHER INFORMATION: first tag sequence: N764

<400> SEQUENCE: 64
caagcagaag acggcatacg agatgccatt gcgtctcgtg ggctcgg    47

<210> SEQ ID NO 65
<211> LENGTH: 47
<212> TYPE: DNA
<213> ORGANISM: Artificial Sequence
<220> FEATURE:
<223> OTHER INFORMATION: first tag sequence: N765

<400> SEQUENCE: 65
caagcagaag acggcatacg agatgagaat acgtctcgtg ggctcgg    47

<210> SEQ ID NO 66
<211> LENGTH: 47
<212> TYPE: DNA
<213> ORGANISM: Artificial Sequence
<220> FEATURE:
<223> OTHER INFORMATION: first tag sequence: N766

<400> SEQUENCE: 66
caagcagaag acggcatacg agatgtaatg acgtctcgtg ggctcgg    47

<210> SEQ ID NO 67
<211> LENGTH: 47
<212> TYPE: DNA
<213> ORGANISM: Artificial Sequence
<220> FEATURE:
<223> OTHER INFORMATION: first tag sequence: N767

<400> SEQUENCE: 67
caagcagaag acggcatacg agatgcttgg atgtctcgtg ggctcgg    47

<210> SEQ ID NO 68
<211> LENGTH: 47
<212> TYPE: DNA
<213> ORGANISM: Artificial Sequence
<220> FEATURE:
<223> OTHER INFORMATION: first tag sequence: N768

<400> SEQUENCE: 68
caagcagaag acggcatacg agatagtata ccgtctcgtg ggctcgg    47

<210> SEQ ID NO 69
<211> LENGTH: 47
<212> TYPE: DNA
<213> ORGANISM: Artificial Sequence
<220> FEATURE:
<223> OTHER INFORMATION: first tag sequence: N769

<400> SEQUENCE: 69
caagcagaag acggcatacg agatgcacgc aagtctcgtg ggctcgg    47

<210> SEQ ID NO 70
<211> LENGTH: 47
<212> TYPE: DNA
<213> ORGANISM: Artificial Sequence
<220> FEATURE:
<223> OTHER INFORMATION: first tag sequence: N770

<400> SEQUENCE: 70
caagcagaag acggcatacg agatccgtcg gagtctcgtg ggctcgg     47

<210> SEQ ID NO 71
<211> LENGTH: 47
<212> TYPE: DNA
<213> ORGANISM: Artificial Sequence
<220> FEATURE:
<223> OTHER INFORMATION: first tag sequence: N771

<400> SEQUENCE: 71
caagcagaag acggcatacg agatatgcct gcgtctcgtg ggctcgg     47

<210> SEQ ID NO 72
<211> LENGTH: 47
<212> TYPE: DNA
<213> ORGANISM: Artificial Sequence
<220> FEATURE:
<223> OTHER INFORMATION: first tag sequence: N772

<400> SEQUENCE: 72
caagcagaag acggcatacg agattcgctg gcgtctcgtg ggctcgg     47

<210> SEQ ID NO 73
<211> LENGTH: 51
<212> TYPE: DNA
<213> ORGANISM: Artificial Sequence
<220> FEATURE:
<223> OTHER INFORMATION: second tag sequence:N501

<400> SEQUENCE: 73
aatgatacgg cgaccaccga gatctacact agatcgctcg tcggcagcgt c     51

<210> SEQ ID NO 74
<211> LENGTH: 51
<212> TYPE: DNA
<213> ORGANISM: Artificial Sequence
<220> FEATURE:
<223> OTHER INFORMATION: second tag sequence:N502

<400> SEQUENCE: 74
aatgatacgg cgaccaccga gatctacacc tctctattcg tcggcagcgt c     51

<210> SEQ ID NO 75
<211> LENGTH: 51
<212> TYPE: DNA
<213> ORGANISM: Artificial Sequence
<220> FEATURE:
<223> OTHER INFORMATION: second tag sequence:N503

<400> SEQUENCE: 75
aatgatacgg cgaccaccga gatctacact atcctcttcg tcggcagcgt c     51

<210> SEQ ID NO 76
<211> LENGTH: 51
<212> TYPE: DNA
<213> ORGANISM: Artificial Sequence
<220> FEATURE:

<223> OTHER INFORMATION: second tag sequence:N504

<400> SEQUENCE: 76
aatgatacgg cgaccaccga gatctacaca gagtagatcg tcggcagcgt c        51

<210> SEQ ID NO 77
<211> LENGTH: 51
<212> TYPE: DNA
<213> ORGANISM: Artificial Sequence
<220> FEATURE:
<223> OTHER INFORMATION: second tag sequence:N505

<400> SEQUENCE: 77
aatgatacgg cgaccaccga gatctacacg taaggagtcg tcggcagcgt c        51

<210> SEQ ID NO 78
<211> LENGTH: 51
<212> TYPE: DNA
<213> ORGANISM: Artificial Sequence
<220> FEATURE:
<223> OTHER INFORMATION: second tag sequence:N506

<400> SEQUENCE: 78
aatgatacgg cgaccaccga gatctacaca ctgcatatcg tcggcagcgt c        51

<210> SEQ ID NO 79
<211> LENGTH: 51
<212> TYPE: DNA
<213> ORGANISM: Artificial Sequence
<220> FEATURE:
<223> OTHER INFORMATION: second tag sequence:N507

<400> SEQUENCE: 79
aatgatacgg cgaccaccga gatctacaca aggagtatcg tcggcagcgt c        51

<210> SEQ ID NO 80
<211> LENGTH: 51
<212> TYPE: DNA
<213> ORGANISM: Artificial Sequence
<220> FEATURE:
<223> OTHER INFORMATION: second tag sequence:N508

<400> SEQUENCE: 80
aatgatacgg cgaccaccga gatctacacc taagccttcg tcggcagcgt c        51

<210> SEQ ID NO 81
<211> LENGTH: 51
<212> TYPE: DNA
<213> ORGANISM: Artificial Sequence
<220> FEATURE:
<223> OTHER INFORMATION: second tag sequence:N509

<400> SEQUENCE: 81
aatgatacgg cgaccaccga gatctacacc tagcgcttcg tcggcagcgt c        51

<210> SEQ ID NO 82
<211> LENGTH: 51
<212> TYPE: DNA
<213> ORGANISM: Artificial Sequence
<220> FEATURE:
<223> OTHER INFORMATION: second tag sequence:N510

<400> SEQUENCE: 82
aatgatacgg cgaccaccga gatctacacc tcacaggtcg tcggcagcgt c        51

-continued

```
<210> SEQ ID NO 83
<211> LENGTH: 51
<212> TYPE: DNA
<213> ORGANISM: Artificial Sequence
<220> FEATURE:
<223> OTHER INFORMATION: second tag sequence:N511

<400> SEQUENCE: 83
aatgatacgg cgaccaccga gatctacacc ttagttgtcg tcggcagcgt c          51

<210> SEQ ID NO 84
<211> LENGTH: 51
<212> TYPE: DNA
<213> ORGANISM: Artificial Sequence
<220> FEATURE:
<223> OTHER INFORMATION: second tag sequence:N512

<400> SEQUENCE: 84
aatgatacgg cgaccaccga gatctacacc ttcctattcg tcggcagcgt c          51

<210> SEQ ID NO 85
<211> LENGTH: 51
<212> TYPE: DNA
<213> ORGANISM: Artificial Sequence
<220> FEATURE:
<223> OTHER INFORMATION: second tag sequence:N513

<400> SEQUENCE: 85
aatgatacgg cgaccaccga gatctacacc ttgtagttcg tcggcagcgt c          51

<210> SEQ ID NO 86
<211> LENGTH: 51
<212> TYPE: DNA
<213> ORGANISM: Artificial Sequence
<220> FEATURE:
<223> OTHER INFORMATION: second tag sequence:N514

<400> SEQUENCE: 86
aatgatacgg cgaccaccga gatctacacg aaccatctcg tcggcagcgt c          51

<210> SEQ ID NO 87
<211> LENGTH: 51
<212> TYPE: DNA
<213> ORGANISM: Artificial Sequence
<220> FEATURE:
<223> OTHER INFORMATION: second tag sequence:N515

<400> SEQUENCE: 87
aatgatacgg cgaccaccga gatctacacg aatgtggtcg tcggcagcgt c          51

<210> SEQ ID NO 88
<211> LENGTH: 51
<212> TYPE: DNA
<213> ORGANISM: Artificial Sequence
<220> FEATURE:
<223> OTHER INFORMATION: second tag sequence:N516

<400> SEQUENCE: 88
aatgatacgg cgaccaccga gatctacacg accaagatcg tcggcagcgt c          51

<210> SEQ ID NO 89
<211> LENGTH: 51
<212> TYPE: DNA
<213> ORGANISM: Artificial Sequence
<220> FEATURE:
<223> OTHER INFORMATION: second tag sequence:N517
```

<400> SEQUENCE: 89
aatgatacgg cgaccaccga gatctacacg atcctcgtcg tcggcagcgt c    51

<210> SEQ ID NO 90
<211> LENGTH: 51
<212> TYPE: DNA
<213> ORGANISM: Artificial Sequence
<220> FEATURE:
<223> OTHER INFORMATION: second tag sequence:N518

<400> SEQUENCE: 90
aatgatacgg cgaccaccga gatctacacg atggacttcg tcggcagcgt c    51

<210> SEQ ID NO 91
<211> LENGTH: 51
<212> TYPE: DNA
<213> ORGANISM: Artificial Sequence
<220> FEATURE:
<223> OTHER INFORMATION: second tag sequence:N519

<400> SEQUENCE: 91
aatgatacgg cgaccaccga gatctacacg attagtgtcg tcggcagcgt c    51

<210> SEQ ID NO 92
<211> LENGTH: 51
<212> TYPE: DNA
<213> ORGANISM: Artificial Sequence
<220> FEATURE:
<223> OTHER INFORMATION: second tag sequence:N520

<400> SEQUENCE: 92
aatgatacgg cgaccaccga gatctacacg cgccttatcg tcggcagcgt c    51

<210> SEQ ID NO 93
<211> LENGTH: 51
<212> TYPE: DNA
<213> ORGANISM: Artificial Sequence
<220> FEATURE:
<223> OTHER INFORMATION: second tag sequence:N521

<400> SEQUENCE: 93
aatgatacgg cgaccaccga gatctacacg gaacagttcg tcggcagcgt c    51

<210> SEQ ID NO 94
<211> LENGTH: 51
<212> TYPE: DNA
<213> ORGANISM: Artificial Sequence
<220> FEATURE:
<223> OTHER INFORMATION: second tag sequence:N522

<400> SEQUENCE: 94
aatgatacgg cgaccaccga gatctacacg gaggaagtcg tcggcagcgt c    51

<210> SEQ ID NO 95
<211> LENGTH: 51
<212> TYPE: DNA
<213> ORGANISM: Artificial Sequence
<220> FEATURE:
<223> OTHER INFORMATION: second tag sequence:N523

<400> SEQUENCE: 95
aatgatacgg cgaccaccga gatctacacg gagtcgctcg tcggcagcgt c    51

<210> SEQ ID NO 96
<211> LENGTH: 51

<212> TYPE: DNA
<213> ORGANISM: Artificial Sequence
<220> FEATURE:
<223> OTHER INFORMATION: second tag sequence:N524

<400> SEQUENCE: 96
aatgatacgg cgaccaccga gatctacacg gcctgtatcg tcggcagcgt c    51

<210> SEQ ID NO 97
<211> LENGTH: 51
<212> TYPE: DNA
<213> ORGANISM: Artificial Sequence
<220> FEATURE:
<223> OTHER INFORMATION: second tag sequence:N525

<400> SEQUENCE: 97
aatgatacgg cgaccaccga gatctacacg gcttaactcg tcggcagcgt c    51

<210> SEQ ID NO 98
<211> LENGTH: 51
<212> TYPE: DNA
<213> ORGANISM: Artificial Sequence
<220> FEATURE:
<223> OTHER INFORMATION: second tag sequence:N526

<400> SEQUENCE: 98
aatgatacgg cgaccaccga gatctacacg gtaattatcg tcggcagcgt c    51

<210> SEQ ID NO 99
<211> LENGTH: 51
<212> TYPE: DNA
<213> ORGANISM: Artificial Sequence
<220> FEATURE:
<223> OTHER INFORMATION: second tag sequence:N527

<400> SEQUENCE: 99
aatgatacgg cgaccaccga gatctacacg gtgttattcg tcggcagcgt c    51

<210> SEQ ID NO 100
<211> LENGTH: 51
<212> TYPE: DNA
<213> ORGANISM: Artificial Sequence
<220> FEATURE:
<223> OTHER INFORMATION: second tag sequence:N528

<400> SEQUENCE: 100
aatgatacgg cgaccaccga gatctacacg tcctacgtcg tcggcagcgt c    51

<210> SEQ ID NO 101
<211> LENGTH: 51
<212> TYPE: DNA
<213> ORGANISM: Artificial Sequence
<220> FEATURE:
<223> OTHER INFORMATION: second tag sequence:N529

<400> SEQUENCE: 101
aatgatacgg cgaccaccga gatctacacg tcgagagtcg tcggcagcgt c    51

<210> SEQ ID NO 102
<211> LENGTH: 51
<212> TYPE: DNA
<213> ORGANISM: Artificial Sequence
<220> FEATURE:
<223> OTHER INFORMATION: second tag sequence:N530

<400> SEQUENCE: 102
aatgatacgg cgaccaccga gatctacacg tgcgtagtcg tcggcagcgt c        51

<210> SEQ ID NO 103
<211> LENGTH: 51
<212> TYPE: DNA
<213> ORGANISM: Artificial Sequence
<220> FEATURE:
<223> OTHER INFORMATION: second tag sequence:N531

<400> SEQUENCE: 103
aatgatacgg cgaccaccga gatctacacg ttaaccttcg tcggcagcgt c        51

<210> SEQ ID NO 104
<211> LENGTH: 51
<212> TYPE: DNA
<213> ORGANISM: Artificial Sequence
<220> FEATURE:
<223> OTHER INFORMATION: second tag sequence:N532

<400> SEQUENCE: 104
aatgatacgg cgaccaccga gatctacacg ttgcaactcg tcggcagcgt c        51

<210> SEQ ID NO 105
<211> LENGTH: 51
<212> TYPE: DNA
<213> ORGANISM: Artificial Sequence
<220> FEATURE:
<223> OTHER INFORMATION: second tag sequence:N533

<400> SEQUENCE: 105
aatgatacgg cgaccaccga gatctacact aattgagtcg tcggcagcgt c        51

<210> SEQ ID NO 106
<211> LENGTH: 51
<212> TYPE: DNA
<213> ORGANISM: Artificial Sequence
<220> FEATURE:
<223> OTHER INFORMATION: second tag sequence:N534

<400> SEQUENCE: 106
aatgatacgg cgaccaccga gatctacact agacttgtcg tcggcagcgt c        51

<210> SEQ ID NO 107
<211> LENGTH: 51
<212> TYPE: DNA
<213> ORGANISM: Artificial Sequence
<220> FEATURE:
<223> OTHER INFORMATION: second tag sequence:N535

<400> SEQUENCE: 107
aatgatacgg cgaccaccga gatctacact aggttgttcg tcggcagcgt c        51

<210> SEQ ID NO 108
<211> LENGTH: 51
<212> TYPE: DNA
<213> ORGANISM: Artificial Sequence
<220> FEATURE:
<223> OTHER INFORMATION: second tag sequence:N536

<400> SEQUENCE: 108
aatgatacgg cgaccaccga gatctacact atggtagtcg tcggcagcgt c        51

<210> SEQ ID NO 109
<211> LENGTH: 51
<212> TYPE: DNA
<213> ORGANISM: Artificial Sequence

```
<220> FEATURE:
<223> OTHER INFORMATION: second tag sequence:N537

<400> SEQUENCE: 109
aatgatacgg cgaccaccga gatctacact atgtgtctcg tcggcagcgt c          51

<210> SEQ ID NO 110
<211> LENGTH: 51
<212> TYPE: DNA
<213> ORGANISM: Artificial Sequence
<220> FEATURE:
<223> OTHER INFORMATION: second tag sequence:N538

<400> SEQUENCE: 110
aatgatacgg cgaccaccga gatctacact attatcttcg tcggcagcgt c          51

<210> SEQ ID NO 111
<211> LENGTH: 51
<212> TYPE: DNA
<213> ORGANISM: Artificial Sequence
<220> FEATURE:
<223> OTHER INFORMATION: second tag sequence:N539

<400> SEQUENCE: 111
aatgatacgg cgaccaccga gatctacact caccgcgtcg tcggcagcgt c          51

<210> SEQ ID NO 112
<211> LENGTH: 51
<212> TYPE: DNA
<213> ORGANISM: Artificial Sequence
<220> FEATURE:
<223> OTHER INFORMATION: second tag sequence:N540

<400> SEQUENCE: 112
aatgatacgg cgaccaccga gatctacact catagtatcg tcggcagcgt c          51

<210> SEQ ID NO 113
<211> LENGTH: 51
<212> TYPE: DNA
<213> ORGANISM: Artificial Sequence
<220> FEATURE:
<223> OTHER INFORMATION: second tag sequence:N541

<400> SEQUENCE: 113
aatgatacgg cgaccaccga gatctacact ccaacaatcg tcggcagcgt c          51

<210> SEQ ID NO 114
<211> LENGTH: 51
<212> TYPE: DNA
<213> ORGANISM: Artificial Sequence
<220> FEATURE:
<223> OTHER INFORMATION: second tag sequence:N542

<400> SEQUENCE: 114
aatgatacgg cgaccaccga gatctacact cctcacttcg tcggcagcgt c          51

<210> SEQ ID NO 115
<211> LENGTH: 51
<212> TYPE: DNA
<213> ORGANISM: Artificial Sequence
<220> FEATURE:
<223> OTHER INFORMATION: second tag sequence:N543

<400> SEQUENCE: 115
aatgatacgg cgaccaccga gatctacact cggcgattcg tcggcagcgt c          51
```

<210> SEQ ID NO 116
<211> LENGTH: 51
<212> TYPE: DNA
<213> ORGANISM: Artificial Sequence
<220> FEATURE:
<223> OTHER INFORMATION: second tag sequence:N544

<400> SEQUENCE: 116
aatgatacgg cgaccaccga gatctacact ctataagtcg tcggcagcgt c        51

<210> SEQ ID NO 117
<211> LENGTH: 51
<212> TYPE: DNA
<213> ORGANISM: Artificial Sequence
<220> FEATURE:
<223> OTHER INFORMATION: second tag sequence:N545

<400> SEQUENCE: 117
aatgatacgg cgaccaccga gatctacact ctcatggtcg tcggcagcgt c        51

<210> SEQ ID NO 118
<211> LENGTH: 51
<212> TYPE: DNA
<213> ORGANISM: Artificial Sequence
<220> FEATURE:
<223> OTHER INFORMATION: second tag sequence:N546

<400> SEQUENCE: 118
aatgatacgg cgaccaccga gatctacact gaggtgatcg tcggcagcgt c        51

<210> SEQ ID NO 119
<211> LENGTH: 51
<212> TYPE: DNA
<213> ORGANISM: Artificial Sequence
<220> FEATURE:
<223> OTHER INFORMATION: second tag sequence:N547

<400> SEQUENCE: 119
aatgatacgg cgaccaccga gatctacact gcaaggttcg tcggcagcgt c        51

<210> SEQ ID NO 120
<211> LENGTH: 51
<212> TYPE: DNA
<213> ORGANISM: Artificial Sequence
<220> FEATURE:
<223> OTHER INFORMATION: second tag sequence:N548

<400> SEQUENCE: 120
aatgatacgg cgaccaccga gatctacact ggagtattcg tcggcagcgt c        51

<210> SEQ ID NO 121
<211> LENGTH: 51
<212> TYPE: DNA
<213> ORGANISM: Artificial Sequence
<220> FEATURE:
<223> OTHER INFORMATION: second tag sequence:N549

<400> SEQUENCE: 121
aatgatacgg cgaccaccga gatctacacg cgaggcctcg tcggcagcgt c        51

<210> SEQ ID NO 122
<211> LENGTH: 51
<212> TYPE: DNA
<213> ORGANISM: Artificial Sequence
<220> FEATURE:
<223> OTHER INFORMATION: second tag sequence:N550

<400> SEQUENCE: 122
aatgatacgg cgaccaccga gatctacact gcgcgcctcg tcggcagcgt c    51

<210> SEQ ID NO 123
<211> LENGTH: 51
<212> TYPE: DNA
<213> ORGANISM: Artificial Sequence
<220> FEATURE:
<223> OTHER INFORMATION: second tag sequence:N551

<400> SEQUENCE: 123
aatgatacgg cgaccaccga gatctacaca ggtggcgtcg tcggcagcgt c    51

<210> SEQ ID NO 124
<211> LENGTH: 51
<212> TYPE: DNA
<213> ORGANISM: Artificial Sequence
<220> FEATURE:
<223> OTHER INFORMATION: second tag sequence:N552

<400> SEQUENCE: 124
aatgatacgg cgaccaccga gatctacacg ccgcatgtcg tcggcagcgt c    51

<210> SEQ ID NO 125
<211> LENGTH: 51
<212> TYPE: DNA
<213> ORGANISM: Artificial Sequence
<220> FEATURE:
<223> OTHER INFORMATION: second tag sequence:N553

<400> SEQUENCE: 125
aatgatacgg cgaccaccga gatctacacc tgttgcctcg tcggcagcgt c    51

<210> SEQ ID NO 126
<211> LENGTH: 51
<212> TYPE: DNA
<213> ORGANISM: Artificial Sequence
<220> FEATURE:
<223> OTHER INFORMATION: second tag sequence:N554

<400> SEQUENCE: 126
aatgatacgg cgaccaccga gatctacact gataccgtcg tcggcagcgt c    51

<210> SEQ ID NO 127
<211> LENGTH: 51
<212> TYPE: DNA
<213> ORGANISM: Artificial Sequence
<220> FEATURE:
<223> OTHER INFORMATION: second tag sequence:N555

<400> SEQUENCE: 127
aatgatacgg cgaccaccga gatctacaca ttggccgtcg tcggcagcgt c    51

<210> SEQ ID NO 128
<211> LENGTH: 51
<212> TYPE: DNA
<213> ORGANISM: Artificial Sequence
<220> FEATURE:
<223> OTHER INFORMATION: second tag sequence:N556

<400> SEQUENCE: 128
aatgatacgg cgaccaccga gatctacacg gacggcttcg tcggcagcgt c    51

<210> SEQ ID NO 129

-continued

```
<211> LENGTH: 51
<212> TYPE: DNA
<213> ORGANISM: Artificial Sequence
<220> FEATURE:
<223> OTHER INFORMATION: second tag sequence:N557

<400> SEQUENCE: 129
aatgatacgg cgaccaccga gatctacacc actctgttcg tcggcagcgt c          51

<210> SEQ ID NO 130
<211> LENGTH: 51
<212> TYPE: DNA
<213> ORGANISM: Artificial Sequence
<220> FEATURE:
<223> OTHER INFORMATION: second tag sequence:N558

<400> SEQUENCE: 130
aatgatacgg cgaccaccga gatctacacg gctgcgttcg tcggcagcgt c          51

<210> SEQ ID NO 131
<211> LENGTH: 51
<212> TYPE: DNA
<213> ORGANISM: Artificial Sequence
<220> FEATURE:
<223> OTHER INFORMATION: second tag sequence:N559

<400> SEQUENCE: 131
aatgatacgg cgaccaccga gatctacacg tcagctctcg tcggcagcgt c          51

<210> SEQ ID NO 132
<211> LENGTH: 51
<212> TYPE: DNA
<213> ORGANISM: Artificial Sequence
<220> FEATURE:
<223> OTHER INFORMATION: second tag sequence:N560

<400> SEQUENCE: 132
aatgatacgg cgaccaccga gatctacaca gccatcatcg tcggcagcgt c          51

<210> SEQ ID NO 133
<211> LENGTH: 51
<212> TYPE: DNA
<213> ORGANISM: Artificial Sequence
<220> FEATURE:
<223> OTHER INFORMATION: second tag sequence:N561

<400> SEQUENCE: 133
aatgatacgg cgaccaccga gatctacaca tgattcatcg tcggcagcgt c          51

<210> SEQ ID NO 134
<211> LENGTH: 51
<212> TYPE: DNA
<213> ORGANISM: Artificial Sequence
<220> FEATURE:
<223> OTHER INFORMATION: second tag sequence:N562

<400> SEQUENCE: 134
aatgatacgg cgaccaccga gatctacacg tctgtcatcg tcggcagcgt c          51

<210> SEQ ID NO 135
<211> LENGTH: 51
<212> TYPE: DNA
<213> ORGANISM: Artificial Sequence
<220> FEATURE:
<223> OTHER INFORMATION: second tag sequence:N563

<400> SEQUENCE: 135
```
aatgatacgg cgaccaccga gatctacaca cgaccactcg tcggcagcgt c          51

<210> SEQ ID NO 136
<211> LENGTH: 51
<212> TYPE: DNA
<213> ORGANISM: Artificial Sequence
<220> FEATURE:
<223> OTHER INFORMATION: second tag sequence:N564

<400> SEQUENCE: 136
aatgatacgg cgaccaccga gatctacacc tccacgctcg tcggcagcgt c          51

<210> SEQ ID NO 137
<211> LENGTH: 51
<212> TYPE: DNA
<213> ORGANISM: Artificial Sequence
<220> FEATURE:
<223> OTHER INFORMATION: second tag sequence:N565

<400> SEQUENCE: 137
aatgatacgg cgaccaccga gatctacacg cggaagttcg tcggcagcgt c          51

<210> SEQ ID NO 138
<211> LENGTH: 51
<212> TYPE: DNA
<213> ORGANISM: Artificial Sequence
<220> FEATURE:
<223> OTHER INFORMATION: second tag sequence:N566

<400> SEQUENCE: 138
aatgatacgg cgaccaccga gatctacacg tacatgttcg tcggcagcgt c          51

<210> SEQ ID NO 139
<211> LENGTH: 51
<212> TYPE: DNA
<213> ORGANISM: Artificial Sequence
<220> FEATURE:
<223> OTHER INFORMATION: second tag sequence:N567

<400> SEQUENCE: 139
aatgatacgg cgaccaccga gatctacact tagccggtcg tcggcagcgt c          51

<210> SEQ ID NO 140
<211> LENGTH: 51
<212> TYPE: DNA
<213> ORGANISM: Artificial Sequence
<220> FEATURE:
<223> OTHER INFORMATION: second tag sequence:N568

<400> SEQUENCE: 140
aatgatacgg cgaccaccga gatctacacc aggatcgtcg tcggcagcgt c          51

<210> SEQ ID NO 141
<211> LENGTH: 51
<212> TYPE: DNA
<213> ORGANISM: Artificial Sequence
<220> FEATURE:
<223> OTHER INFORMATION: second tag sequence:N569

<400> SEQUENCE: 141
aatgatacgg cgaccaccga gatctacaca tatcgtctcg tcggcagcgt c          51

<210> SEQ ID NO 142
<211> LENGTH: 51
<212> TYPE: DNA

```
<213> ORGANISM: Artificial Sequence
<220> FEATURE:
<223> OTHER INFORMATION: second tag sequence:N570

<400> SEQUENCE: 142
aatgatacgg cgaccaccga gatctacact ggccaggtcg tcggcagcgt c        51

<210> SEQ ID NO 143
<211> LENGTH: 51
<212> TYPE: DNA
<213> ORGANISM: Artificial Sequence
<220> FEATURE:
<223> OTHER INFORMATION: second tag sequence:N571

<400> SEQUENCE: 143
aatgatacgg cgaccaccga gatctacact agagagctcg tcggcagcgt c        51

<210> SEQ ID NO 144
<211> LENGTH: 51
<212> TYPE: DNA
<213> ORGANISM: Artificial Sequence
<220> FEATURE:
<223> OTHER INFORMATION: second tag sequence:N572

<400> SEQUENCE: 144
aatgatacgg cgaccaccga gatctacacg acacgcttcg tcggcagcgt c        51

<210> SEQ ID NO 145
<211> LENGTH: 34
<212> TYPE: DNA
<213> ORGANISM: Artificial Sequence
<220> FEATURE:
<223> OTHER INFORMATION: first long-chain sequence of first adaptor

<400> SEQUENCE: 145
gtctcgtggg ctcggagatg tgtataagag acag                           34

<210> SEQ ID NO 146
<211> LENGTH: 19
<212> TYPE: DNA
<213> ORGANISM: Artificial Sequence
<220> FEATURE:
<223> OTHER INFORMATION: first short-chain sequence of first adaptor

<400> SEQUENCE: 146
ctgtctctta tacacatct                                            19

<210> SEQ ID NO 147
<211> LENGTH: 33
<212> TYPE: DNA
<213> ORGANISM: Artificial Sequence
<220> FEATURE:
<223> OTHER INFORMATION: second long-chain sequence of second adaptor

<400> SEQUENCE: 147
tcgtcggcag cgtcagatgt gtataagaga cag                            33

<210> SEQ ID NO 148
<211> LENGTH: 19
<212> TYPE: DNA
<213> ORGANISM: Artificial Sequence
<220> FEATURE:
<223> OTHER INFORMATION: second short-chain sequence of second adaptor

<400> SEQUENCE: 148
ctgtctctta tacacatct                                            19
```

```
<210> SEQ ID NO 149
<211> LENGTH: 21
<212> TYPE: DNA
<213> ORGANISM: Artificial Sequence
<220> FEATURE:
<223> OTHER INFORMATION: sequence 1 of first primer

<400> SEQUENCE: 149
caagcagaag acggcatacg a                                              21

<210> SEQ ID NO 150
<211> LENGTH: 20
<212> TYPE: DNA
<213> ORGANISM: Artificial Sequence
<220> FEATURE:
<223> OTHER INFORMATION: sequence 1 of second primer

<400> SEQUENCE: 150
aatgatacgg cgaccaccga                                                20

<210> SEQ ID NO 151
<211> LENGTH: 21
<212> TYPE: DNA
<213> ORGANISM: Artificial Sequence
<220> FEATURE:
<223> OTHER INFORMATION: sequence 2 of first primer

<400> SEQUENCE: 151
gttcgtcttc tgccgtatgc t                                              21

<210> SEQ ID NO 152
<211> LENGTH: 20
<212> TYPE: DNA
<213> ORGANISM: Artificial Sequence
<220> FEATURE:
<223> OTHER INFORMATION: sequence 2 of second primer

<400> SEQUENCE: 152
ttactatgcc gctggtggct                                                20
```